United States Patent [19]

Itoh et al.

[11] Patent Number: 5,656,811
[45] Date of Patent: Aug. 12, 1997

[54] METHOD FOR MAKING SPECIMEN AND APPARATUS THEREOF

[75] Inventors: Fumikazu Itoh, Fujisawa; Toshihiko Nakata, Hiratsuka; Tohru Ishitani, Hitachinaka; Akira Shimase, Yokosuka; Hiroshi Yamaguchi, Fujisawa; Takashi Kamimura, Yokosuka, all of Japan

[73] Assignee: Hitachi, Ltd., Tokyo, Japan

[21] Appl. No.: 490,423

[22] Filed: Jun. 14, 1995

[30] Foreign Application Priority Data

Jun. 14, 1994 [JP] Japan .................................. 6-132241

[51] Int. Cl.$^6$ .................................................. H01J 37/30
[52] U.S. Cl. ........................ 250/309; 250/310; 250/492.21
[58] Field of Search .................................. 250/309, 307, 250/397, 492.21

[56] References Cited

U.S. PATENT DOCUMENTS

| | | | |
|---|---|---|---|
| 3,699,334 | 10/1972 | Cohen et al. | |
| 3,840,721 | 10/1974 | Monk | 250/491.1 |
| 4,672,196 | 6/1987 | Canino | 250/225 |
| 5,055,696 | 10/1991 | Haraichi et al. | 250/492.2 |
| 5,315,123 | 5/1994 | Itoh et al. | 250/491.1 |
| 5,331,161 | 7/1994 | Ohdomarti et al. | 250/309 |
| 5,371,582 | 12/1994 | Toba | 356/73 |

FOREIGN PATENT DOCUMENTS

| | | |
|---|---|---|
| 2203509 | 5/1974 | France . |
| 56-94629 | 7/1981 | Japan . |
| 56-130921 | 10/1981 | Japan . |
| 58-167775 | 10/1983 | Japan . |
| 58-184247 | 10/1983 | Japan . |
| 60-64228 | 4/1985 | Japan . |
| 61-130848 | 6/1986 | Japan . |
| 4-76437 | 3/1992 | Japan . |
| 4-2430138 | 9/1992 | Japan . |
| 4-361132 | 12/1992 | Japan . |
| 5-15981 | 1/1993 | Japan . |
| 5-231998 | 9/1993 | Japan . |
| 2 010 577 | 6/1979 | United Kingdom . |
| 2 105 858 | 3/1983 | United Kingdom . |

OTHER PUBLICATIONS

"J. Vac. Sci. Technol. B11(3)", (May/Jun. 1993), pp. 531–535.

"An Updated Gas Source Focused Ion Beam Instrument for TEM Specimen Preparation", R. Alani, et al, Database Inspec, Institute of Electrical Engineers, Stevenage, GB, Inspec No. 4423033, Mat. Res. Soc. Symp. Proc., vol. 254, 1992.

"Specimen Preparation for Transmission Electron Microscopy of Materials—III", Symposium, Boston, MA, USA 5–6 Dec. 1991, Mat. Res. Soc. Symp. Proc., vol. 261, pp. 65–78.

Primary Examiner—Bruce Anderson
Attorney, Agent, or Firm—Antonelli, Terry, Stout & Kraus, LLP

[57] ABSTRACT

A method for making a specimen for use in observation through a transparent electron microscope, includes a step of milling part of the specimen into a thin film part, which can be observed through a transparent electron microscope, by scanning and irradiating a focused ion beam onto the specimen, a step of observing a mark for detection of a position provided on the specimen as a secondary charged particle image by scanning and irradiating a charged particle beam onto the specimen without irradiating the charged particle beam onto the portion to be milled into the thin film part during the milling, and a step of compensating for positional drift of the focused ion beam during milling in accordance with a result of the observation. The method is carried out by an apparatus which includes irradiation area control means for controlling an irradiation area of the focused ion beam onto the specimen so that a surface of the specimen to be milled into the thin film part is not included in the secondary charged particle image when the secondary charged particle image of the surface, on which the mark for detecting the milling position of the specimen is formed, is displayed by the secondary charged particle image during milling part of the specimen, and compensation means for compensating the positional drift of the focused ion beam during milling in accordance with the mark for detecting the milling position.

27 Claims, 15 Drawing Sheets

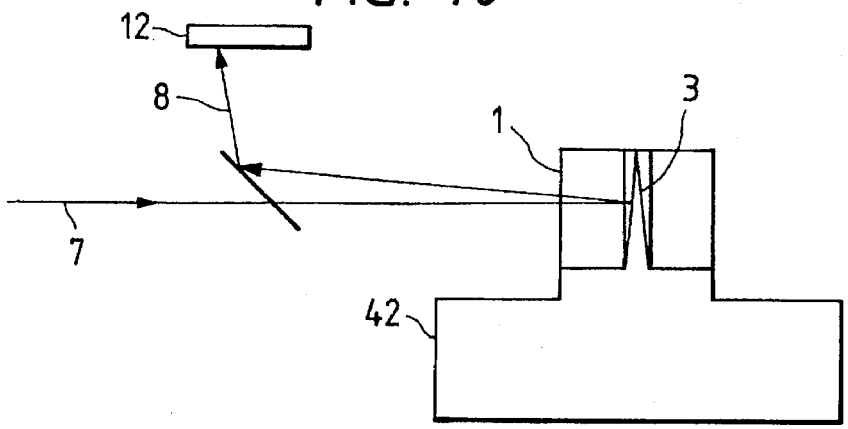
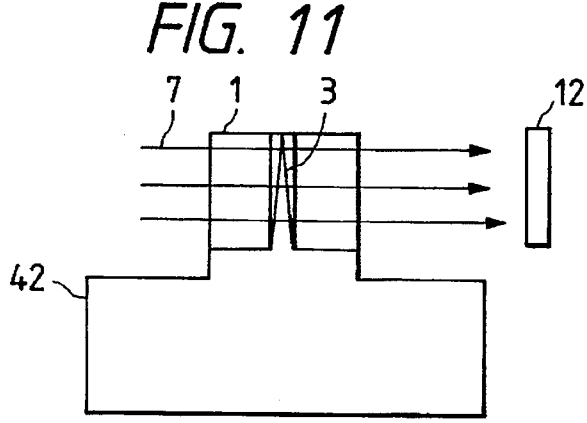
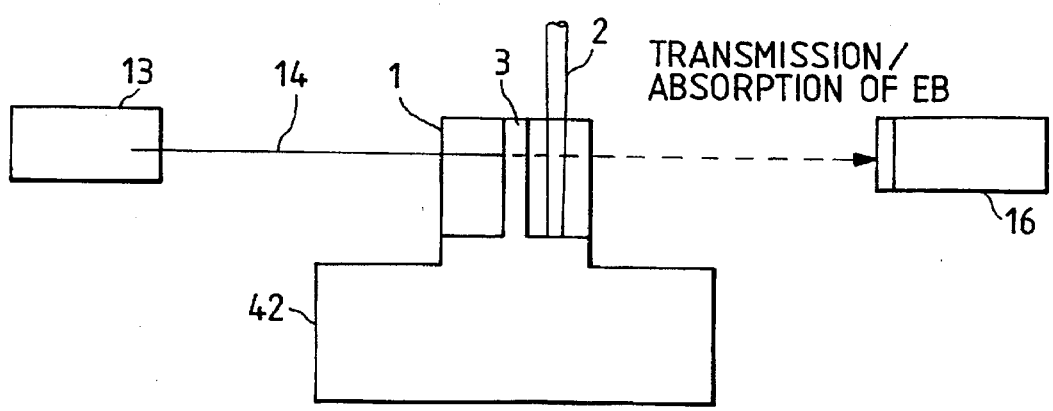

ARROW A VIEW

METHOD FOR MAKING SPECIMEN AND APPARATUS THEREOF

BACKGROUND OF THE INVENTION

The present invention relates to a method of making a specimen for observing a specific portion of a semiconductor device through use of a transparent electron microscope and, more particularly, to a method of and an apparatus for making a specimen by milling with a focused ion beam.

Recently, focused ion beam (hereafter referred to as "FIB") milling has been used for making specimens of specific portions of semiconductor devices for use on a transparent electron microscope thereafter referred to as "TEM") in analyses of a gate portion of a specific memory cell and an interface of a metal contact of a specific contact hole of a semiconductor device. An example of such a method will be described below with reference to the drawings. As shown, for example, in FIG. 2, a surface of a specimen 42 is polished by a polishing apparatus to form a protruding part 1 of 30 to 100 µm (typically, 50 µm) in width and 10 to 100 µm (typically, 50 µm) in height so that a portion to be observed is positioned at the center of this protruding part.

As shown in FIG. 3, portions of both sides of the protruding part 1 are removed to a depth of d=3 to 10 µm and a width of w=4 to 15 µm using a focused ion beam 2 so as to leave a thin film part 3 having a desired thickness t at the center of the protruding part. The protruding part is milled so that a portion to be observed is formed in this thin film part 3. The thickness t of this thin film part 3 needs to be approximately 100 nm or less to carry out a TEM observation. To leave such a small thickness, the protruding part is processed to leave a film having a thickness of 1 µm by using a focused ion beam of approximately 0.5 to 1 µm in beam diameter in an initial stage of processing, and the thin film part 3 with thickness t is further gradually milled by using a thinner beam of approximately 0.1 µm or less in beam diameter to finish a specimen for TEM observation, which is provided with a final thickness of approximately 100 nm or less.

A first prior method related to the above-described type of processing, for example, is described in Japanese Patent Application Disclosure Hei 5-15981, which discloses a method of milling a specimen for use in SEM observation of a cross section, which method is adapted to mill a mark so as to make it possible to control a position of a cross section to be finally obtained and is adapted to set a finishing position by using this scanning ion microscope image (SIM image).

As a second prior method, the "J. Vac. Sci. Technol. Bll, (3) (May/June), pp 531 to 535, 1993" published by the U.S. Society of Vacuum, discloses a method of milling a specimen for use in TEM observation by which an electron beam is irradiated on the specimen during FIB processing and the thickness of a film which is formed by milling is obtained by observing secondary electrons or reflecting electrons generated therefrom.

In most cases, the positional drift of the focused ion beam 2 is approximately 0.1 µm to 0.5 µm/10 minutes. Therefore, if the laser beam drifts to the center of the thin film part 3, as shown in a plan view of a relevant part of a milled surface of the specimen in FIG. 4, the thin film part 3 is often excessively milled and the portion to be observed is inadvertently milled off.

When the thickness t of the thin film part 3 approaches 200 nm, it becomes difficult to identify the thin film part 3 from a scanning ion image and to set a milling area 5, and therefore there is a risk that the portion to be observed may be inadvertently milled away and damaged. In the case of the first prior method, marks 6a and 6b are provided in an area shown as an observing area 4 of the thin film part 3 in FIG. 4, and a milling area 5 can be determined by observing scanning ion microscope images (SIM image) of these marks. However, there has been a risk that, when the thickness of the thin film part 3 approaches approximately 200 nm, the top part of the thin film part 3 may be milled while the scanning ion image is observed and the thin film part 3 may be excessively thinned.

In the case of the second prior method, high costs are required to provide an electron gun for the SEM, a power supply and a controller, and it is spatially difficult to simultaneously reduce sufficiently the operating distance of the focused ion beam optics and that of the electron beam optics, since the electron gun is arranged nearby the workpiece. Therefore, installation of the SEM on a practical focused ion beam milling unit includes two problems, that is, the high price of the apparatus and the difficulty in focusing the laser beam to obtain sufficiently thin beam.

In the above prior method, practical means for observing the thickness distribution of the thin film part and means for detecting an electron beam which passes through the thin film part are employed. For this reason, the prior methods include a problem in that, if a specimen for TEM observation is made by using an ordinary focused ion beam milling machine, a failure may be often repeated, the work efficiency is extremely low and a lot of time is required to obtain the data for TEM observation. In addition, there is another problem in that, if only one specimen is available, it cannot be milled to be sufficiently thin due to a fear of probable breakage.

SUMMARY OF THE INVENTION

Objects of the present invention are to solve the above-described problems of the prior methods. For this purpose, a first object is to provide a method of making a specimen capable of certainly finishing a TEM specimen with an appropriate thickness by use of focused ion beam milling without fail, and a second object is to provide a useful and economical specimen milling apparatus.

To attain the above objects, the present invention is adapted to (1) provide a mark for measuring a positional drift of a focused ion beam on a protruding part at a position outside of the thin film part to be milled to a predetermined thickness, observe this mark with the focused ion beam at an appropriate frequency during milling so that an observing area does not include the thin film part, and measure and compensate a positional drift of the beam, (2) prevent excessive milling by monitoring the thickness of the thin film part during milling with, for example, a light beam, which is more economical than an electron beam, and (3) measure the thickness distribution of the thin film part by scanning the thin film part 3 with the light beam or an electron beam. The following describes in detail a practical means for attaining the objects of the present invention.

The first object of the present invention is attained by a method of milling a workpiece, in forming a specimen with a thin film by use of focused ion beam milling, while compensating for any positional drift of the focused ion beam by observing a mark for measuring the positional drift of the focused ion beam provided on the workpiece, a predetermined number of times as a scanning secondary charged particle microscope image. The method is a specimen making method which comprises the steps of providing the mark at a position outside of the thin film part, which is to be milled to a predetermined thickness, for arranging the mark so that both one side of the milling area and one side of the observing area with the focused ion beam are coincident with the milled surface of the thin film, or so that one side of the observing area does not come in contact with the milled surface and is kept away in the opposite direction, and for forming the thin film part.

It is preferable to compensate for the positional drift of the ion beam and monitor the thickness of a remaining film portion during milling with the focused ion beam. In other words, the thin film part is formed by accurately milling the workpiece to the predetermined film thickness while monitoring the thickness of the thin film part.

Various film thickness measuring methods such as, for example, (1) optical interferometry, (2) a method for detecting a transparent light intensity of a slit-shaped beam, (3) a method for detecting a transparent image of a scanning laser beam, (4) a method for detecting the transparent light intensity of an electron beam, (5) a method for detecting the transparent image of the scanning electron beam and (6) a method for detecting a distortion of the thin film caused by irradiation of a pulse laser beam, are used as a film thickness monitoring method. Particularly, the film thickness measuring method using optical measuring means is practical and preferable.

For milling a workpiece with the focused ion beam, the method can be adapted to slightly tilt a surface to be milled on the workpiece and monitor the tilting angle. Since the current density distribution of the focused ion beam has a tail and a milled end surface of the workpiece is slightly tilted due to an effect of such tail, even when the beam is reduced in diameter to be thinner, monitoring of the tilting as described above is required to compensate for the latter tilting of the milled surface. Therefore, the tilting angle of the milled surface of the workpiece in this case should meet the characteristic (the tail of the current density distribution) of the focused ion beam to be used. For example, a method of measuring a reflection angle of light irradiated onto the milled surface can easily be adopted for monitoring the tilt of this milled surface.

The first object of the present invention can be also attained, in milling a specimen by the above-described specimen making method, by use of a focused ion beam milling method which is adapted to form a surface to be milled by irradiating a focused ion beam onto the specimen, by scanning the surface to be milled with the electron beam at a scanning velocity largely differing from the scanning velocity of the focused ion beam, by detecting secondary charged particles from the specimen, by eliminating noise by passing signals of the detected secondary charged particles through a filter of a high or low frequency, and by displaying a scanning electron microscope image or a scanning ion microscope image by using the signals from which noises have been eliminated. In this case, the thickness of the milled film can be measured from the transparent electron beam which has passed the milled surface and the workpiece can be accurately milled to a predetermined target thickness while monitoring the film thickness. The thickness distribution of the thin film part can be measured by scanning the surface, which has been milled by the focused ion beam, with a light beam or an electron beam.

The following describes the beam irradiating conditions when the specimen is milled with a focused ion beam and those when a secondary charged particle image is obtained by scanning with the beam. Though usually the beam intensity is fixed and the scanning velocity is changed, care is taken to reduce the scanning velocity to increase the irradiation dose per unit area and to improve the efficiency in milling and, on the contrary, raise the scanning velocity to reduce the irradiation dose and protect the specimen wherever possible in obtaining the secondary charged particle image. In case of fixing the scanning velocity, the dose is changed by controlling an ion source, but the former scanning velocity control method is practical and preferable in view of the ease in determination of a configuration of the apparatus.

The second object of the present invention is attained by using a specimen making apparatus comprising means for changing over the observing area and the milling area for ion beam scanning so that respective designated sides of the observing area and the milling area match or the one side of the observing area remains at a relative position retracted from the one side of the milling area in an opposite direction to the milled surface of the specimen. The focused ion beam milling apparatus at least comprises ① optics for focusing an ion beam which is provided with a high brightness ion source, focusing optics for focusing the ion beam to an extremely small spot, and a deflector for deflection-scanning the ion beam on the specimen, ② a secondary charged particle observing system which is provided with a secondary charged particle detector for detecting secondary charged particles from the specimen to obtain a scanning secondary charged particle microscope image and an imaging device for a scanning secondary charged particle microscope image, ③ a stage for supporting and moving the specimen arranged in a sample vacuum chamber, and ④ a vacuum pumping system.

In the above specimen making apparatus, it is preferable to provide a means for monitoring the thickness of the thin film specimen (workpiece) which is mounted on a stage arranged in the specimen vacuum chamber and is being milled.

As the means for monitoring the thickness of the thin film there is used one of, for example, (1) means provided with an optical irradiation device and a light interferometer, (2) means provided with an optical irradiation device and an optical transparent detector, (3) means provided with a slit-shaped light irradiation device and an optical transparent detector, (4) means provided with a scanning laser beam irradiation device, an optical transparent detector and an imaging device for display of a scanning electron transparent image, (5) means provided with an electron beam gun and an electron beam transparent detector, (6) means provided with a scanning electron beam irradiation device, an electron beam transmission detector and an imaging device for display of a scanning electron transparent image, and (7) means provided with a pulse laser generator and an interferometer for detecting a distortion of the thin film due to irradiation thereof by a pulse laser.

In any one of the above-described means for monitoring the film thickness, the light or electron irradiation part and the detector can be fixed to the specimen stage.

In the above specimen making apparatus, it is preferable to provide a means for monitoring a tilting angle of the milled surface of the thin film specimen (workpiece) which is mounted on a stage arranged in the specimen vacuum chamber and is being milled. This monitoring means comprises, for example, a light irradiation device and a device for detecting a reflecting position of the light.

The above specimen making apparatus can be provided with a focused electron beam irradiation device which is constructed to permit irradiation onto the thin film specimen during focused ion beam milling, a controller for scanning the electron beam at a scanning velocity independent of the scanning velocity of the focused ion beam, a secondary charged particle detector for detecting secondary charged particles from the specimen, a circuit for filtering the signals of detected secondary charged particles at a high or low frequency, and an imaging device for displaying a scanning electron microscope image or a scanning ion microscope image by means of the filtered signals. Thus, the thickness and thickness distribution of the thin film to be milled can be determined, and therefore high precision milling with a more uniformly controlled thickness distribution can be carried out by feeding back this thickness information for controlling the thickness during focused ion beam milling.

The mark for measuring the positional drift of the beam is observed with the focused ion beam so that the observing area does not include the thin film part and therefore the observing part can be protected from being milled. In addition, the thickness of the thin film part can be monitored and therefore the milling position of the focused ion beam can be accurately set.

BRIEF DESCRIPTION OF THE DRAWINGS

FIG. 10 is a diagrammatic view of a specimen showing an example of a method of monitoring the thickness of a thin film part according to the present invention;

FIG. 11 is a diagrammatic view of a specimen showing an example of a method of monitoring the thickness of a thin film part according to the present invention;

FIG. 12 is a diagrammatic view of a specimen showing an example of a method of monitoring the thickness of a thin film part according to the present invention;

DESCRIPTION OF THE PREFERRED EMBODIMENTS

First of all, a principle involving the observation of position marks according to the present invention will be described in detail with reference to the drawings.

Figure 4:
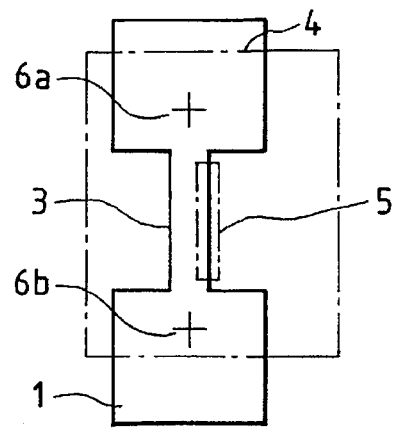
FIG. 4 is a plan view of the specimen showing a known method of observing a scanning charged particle microscopic image (SIM image) of the specimen.

As shown in FIG. 4, in the known method, while the thickness of the thin film part 3 is still sufficiently larger than a predetermined target thickness, the observing area 4 is set so that the thin film part 3 is observed at the center thereof, as described heretofore. Then, the milling area 5 is set and milling is carried out. However, if the observing area is set as shown in FIG. 4, when the milling has progressed and the thin film part 3 is sufficiently thin, it may be found that the top portion of the thin film part 3 has been milled off.

Figure 5A:
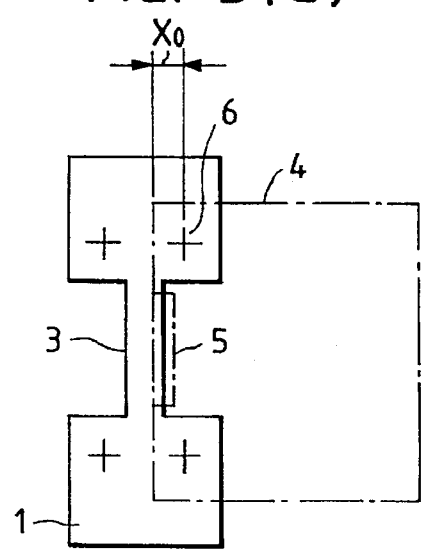
FIGS. 5(a) and 5(b) are plan views of the specimen showing a method for observing an SIM image of the specimen according to the present invention.
Figure 5B:
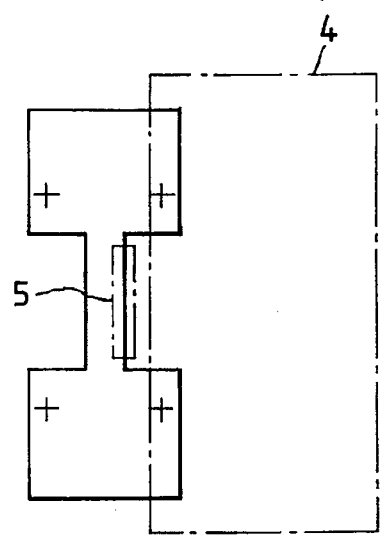

Therefore, the present invention takes a different approach, as shown in FIG. 5(a), in positioning the observing area 4 and the milling area 5, so that the left-side end of the milling area 5 is aligned with the left-side end of the observing area 4, as seen in FIG. 5(b), or the position of the observing area 4 is determined by shifting the left-side end thereof in a direction opposite to the milled surface, for observing the marks 6 on the scanning ion microscope image to measure the positional drift of the beam during milling, for example, on the right side of the thin film part 3. In milling the left side of the thin film part, the relative positions are reversed and therefore the position of the observing area 4 is determined by aligning the right-side end of the observing area 4 with the right-side end of the milling area 5 or by shifting the observing area 4 away from the right-side end of the milling area 5. In this case, an important point is the positioning of the observing area 4 at the side where the thin film part 3 is milled, and the observing area 4 should not protrude toward the thin film part 3 from a position where it is maintained in contact with the milled surface of the thin film part 3 in the milling area 5. In FIG. 5(a), the left-side ends of the milling area 5 and the observing area 4 are aligned.

Figure 6:
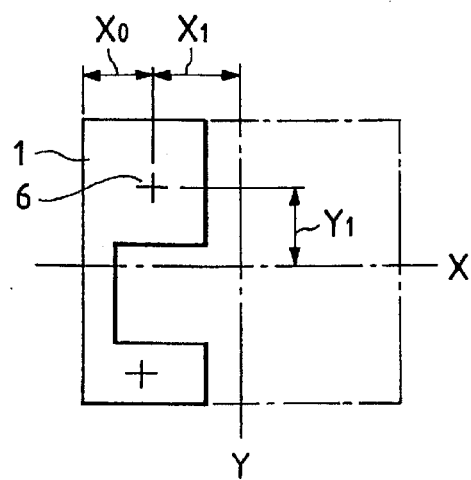
FIG. 6 is a diagram of the SIM image of the specimen in an initial stage of milling according to the present invention.

The scanning ion microscope image observed in the initial stage of milling of one side of a thin film part is shown in FIG. 6. The marks 6 are provided in advance by using a focused ion beam at the positions which are included in this observing area 4. It is important to provide these marks 6 so that they do not fall outside of the observing area 4, and are always positioned within the observing area 4, but outside of the area of the thin film part 3. In general, the width of the cross of this mark 6 should preferably be approximately 0.1 $\mu$m.

Figure 7:
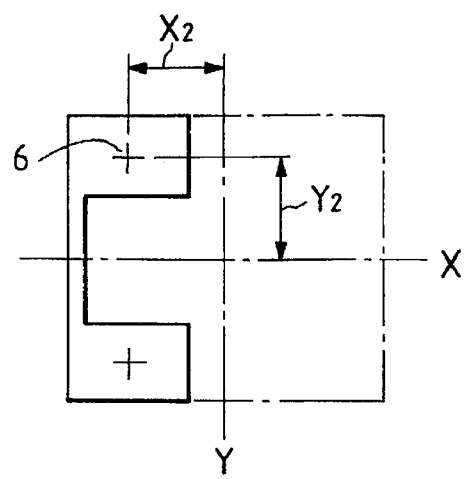
FIG. 7 is a diagram of the SIM image of the specimen on which milling is further progressed.

An example of the scanning ion microscopic image observed during a more advanced stage of milling is shown in FIG. 7. Expressions $dx=x_2-x_1$ and $dy=y_2-y_1$ derived from the positions $x_1$ and $y_1$ of the mark 6 from reference axes x and y shown in FIG. 6, and the positions $x_2$ and $y_2$ shown in FIG. 7, represent the positional drift of the beam. The position of the beam is shifted as much as dx and dy by deflecting the beam. A preferable frequency of observation is one to five minutes, depending on the stability of the beam.

The anticipated objects of the present invention can be attained with the above configuration. In other words, the thin film part can be accurately milled by avoiding irradiation of the focused ion beam onto the thin film part, even when there is positional drift of the focused ion beam, while observing the mark provided on the specimen in the SIM image. Moreover, an appropriate infeed amount of milling can be set with an inexpensive apparatus by using a light beam as a means for monitoring the thickness of the thin film part during milling. In addition, since the thickness distribution of the thin film part, which is light with reference to the light beam or an electron beam, can be measured, therefore, the TEM specimen can be finished to an appropriate thickness within a short period of time with a high percentage of success and the efficiency of TEM observation can be greatly raised.

Embodiments of the present invention based on the above-described principle will be described below.

An example of the specimen making method using ion beam milling according to the present invention will be described in detail along with a description of how to carry out milling of the workpiece, and including methods for observing the mark for measuring the positional drift of the ion beam and for effecting compensation of the positional drift of the beam, with reference to FIGS. 5(a) to 7.

In FIG. 5(a), the protruding part 1 of the specimen is roughly milled so that the thin film part 3 to be formed on the protruding part 1 of the specimen has a thickness of approximately 2 $\mu$m, which is sufficiently larger than the final finish thickness of 100 to 200 nm. Before beginning the finish milling, the SIM image of the observing area 4 shown in FIG. 5(a) is set so that the left end of the SIM image is aligned with the target finished surface boundary (the edge of the milling area 5) of the thin film part 3. On the SIM image shown in FIG. 6, a distance $x_0$ between the left end of the image (that is, the boundary of the target finished surface) and the mark 6 in the x direction is measured in advance. At the same time, distances $x_1$ and $y_1$ between the center line of the image and the mark are measured in advance for each mark.

A milling area for which the infeed amount is predetermined to be approximately 1 $\mu$m is set on the SIM image shown in FIG. 6 and milling is carried out. When the milling is finished, the SIM image is observed again. In this case, if the position of the mark 6 is presented as $x_2$ and $y_2$ (provided, $x_2 \neq x_1$ and $y_2 \neq y_1$) as shown in FIG. 7, the positional drift of the beam appears as $x_2-x_1$ and $y_2-y_1$, and therefore the observing area 4 has been translated in parallel by as much as $x_2-x_1$ and $y_2-y_1$ in x and y directions, respectively. Thus, the left-side of the image is aligned with the target finish-milled surface. It is checked again that the distance between the finish-milled surface and the mark is $x_0$.

Further, the infeed amount is set to 0.5 $\mu$m. In other words, the thickness of the remaining film is 2 $\mu$m–1 $\mu$m–0.5 $\mu$m=0.5 $\mu$m. Then, milling is carried out again. The infeed amount is gradually reduced to reach the target finish-milled surface by repeating this operating procedure. Thus, the fear of milling off the thin film part 3 is eliminated by setting the observing area 4 so that the area 4 does not cover any part of the thin film part 3, which is to be retained and high precision milling can be carried out by measuring a deviation of the mark during milling, while compensating for any positional drift of the beam.

A method of monitoring the thickness and the thickness distribution of the thin film part 3 will be described with reference to FIGS. 1 and 8 to 19.

Figure 1:
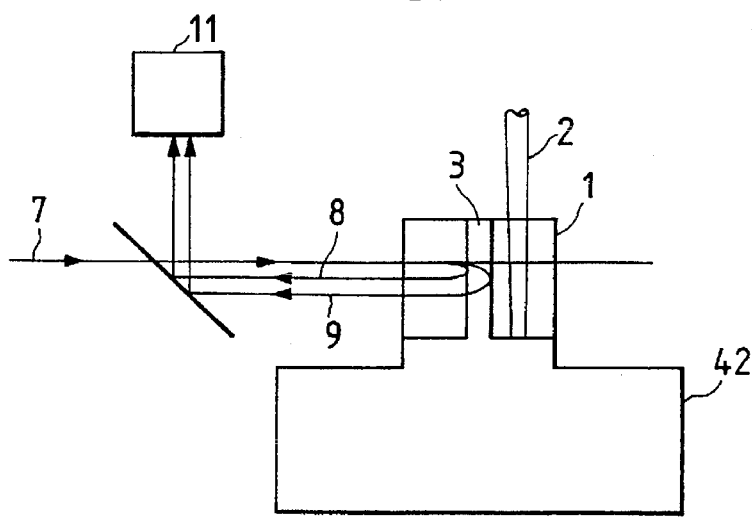
FIG. 1 is a schematic view of a specimen showing an example of a method of monitoring the thickness of a thin film part, which forms an embodiment of the present invention.
Figure 2:
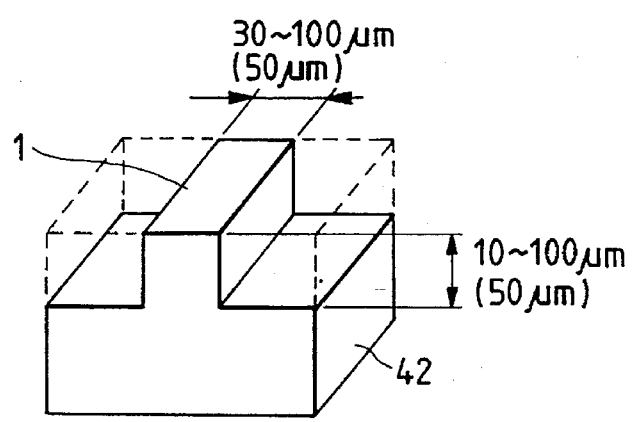
FIG. 2 is a perspective view of a specimen.

FIG. 1 shows a schematic view of optics for measuring the thickness of a thin film part 3 being milled with a focused ion beam 2. A probe light beam 7 is irradiated onto the milled surface to measure the thickness of the thin film part 3 of the specimen 42 as shown. A light beam 8 reflected from the surface of the thin film part 3 and a light beam 9 reflected from the opposite side surface are caused to interfere and the thickness of the thin film part is measured by observing variations of the interference which occurs along milling surface using an interferometer 11.

Figure 8:
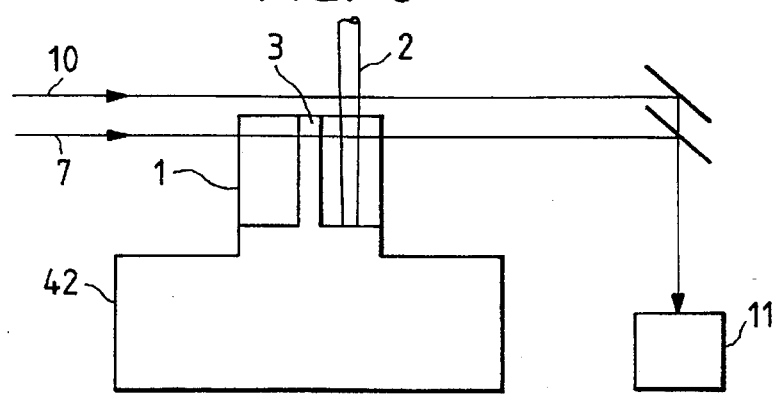
FIG. 8 is a diagrammatic view of a specimen showing an example of a method of monitoring the thickness of a thin film part according to the present invention.

FIG. 8 also shows a schematic view of optics for measuring the thickness of the thin film part 3 being milled with the focused ion beam 2. In this case, the probe light beam 7 is transmitted through the thin film part 3, as shown, and is forced to interfere with a reference light beam 10 which is not transmitted through the thin film part. The thickness is measured by detecting a phase deviation of the probe light due to the thin film part 3. In FIGS. 1 and 8, the probe light 7 needs to pass through the thin film part, and therefore an infrared ray is preferable when the specimen is made of silicon.

Figure 9:
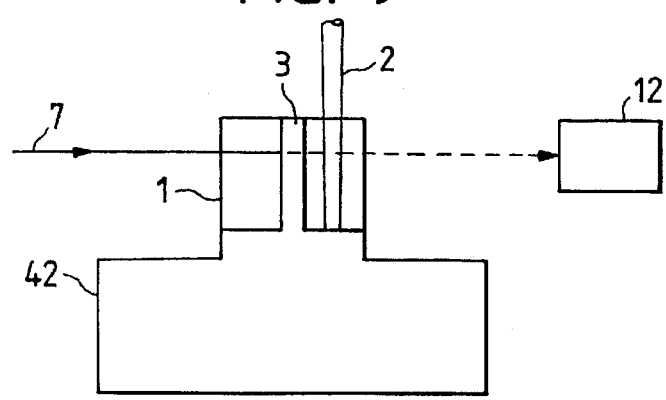
FIG. 9 is a diagrammatic view of a specimen showing an example of a method of monitoring the thickness of a thin film part according to the present invention.

FIG. 9 also shows a schematic view of optics for measuring the thickness of the thin film part 3 being milled with the focused ion beam 2. The probe light beam 7 having a wavelength which is absorbed by the thin film part 3 is passed through the thin film part 3, as shown, and the thickness is measured by measuring the intensity of the light which has been transmitted through the thin film part, using a measuring instrument 12, such as a photomultiplier. In this case, a shorter wavelength is better, and the wavelength should be determined in accordance with the type of material of the specimen.

The side wall of the thin film part 3 tends to be tilted, as shown in FIG. 10. This tilting angle appears as a tail of a current distribution of the ion beam, as described below, and it is important for high precision milling to take into consideration this tail and the tilting angle of the side wall of the thin film part 3. The position of the reflected light beam 8 and the angle of the side wall of the thin film part 3 can be obtained by using a laser beam as the focused probe light and by detecting the laser beam 8 reflected from the side wall of the thin film part 3 with an array detector 12.

FIG. 11 shows a similar method to that shown in FIG. 10 and this method is intended to measure the intensity distribution of the probe light beam 7 as a slit-shaped beam using the array detector 12 and to detect the thickness distribution of the thin film part 3, that is, an excessively thinned top part thereof in most cases.

In FIG. 9, the focused laser beam can be used as the probe light beam 7 and a transparent image of the scanning electron beam can be obtained by scanning the laser beam in the area of the thin film part 3.

FIG. 12 shows an example of measuring the thickness of the thin film part 3 by detecting a transparent electron beam, which is obtained by impinging the electron beam 14 from a focusing electron gun 13 onto the thin film part 3, using an electron beam detector 16 such as a Faraday cup or a scintillator. An appropriate transparent light intensity can be obtained by adjusting an energy of the electron beam 14. In a case where the thin film part 3 is formed of a plurality of materials which have substantially different transmissivities to the electron beam 14, a measurement of an average transparent intensity of the electron beam through the thin film part is insufficient to check the thickness. Therefore, the thickness distribution can be measured by scanning of the electron beam 14. There is an effect that the TEM image can be observed during milling with the focused ion beam by using the same construction as the transparent electron microscope.

Figure 13:
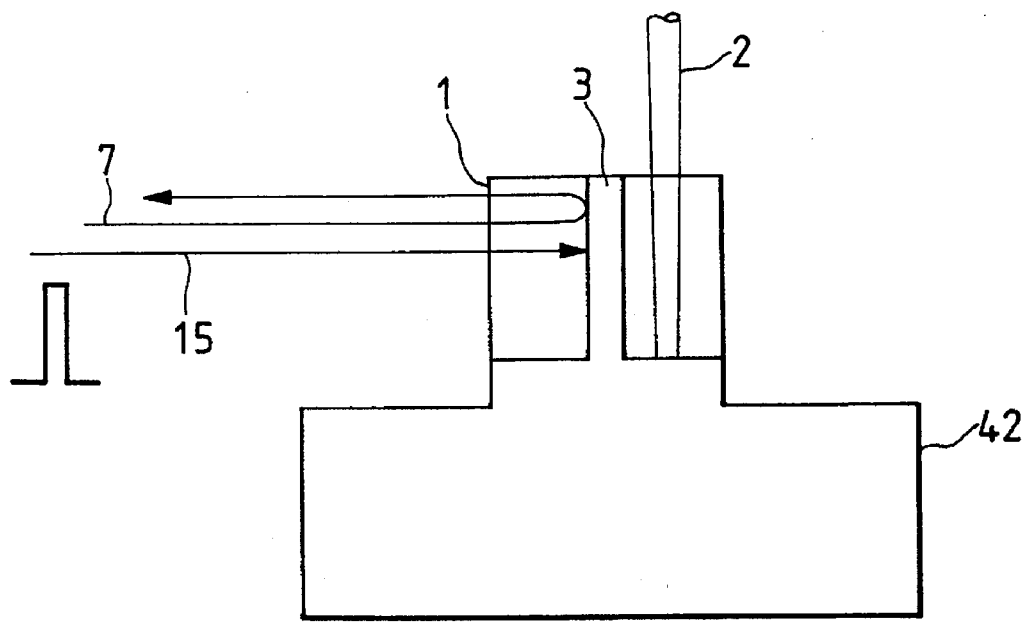
FIG. 13 is a diagrammatic view of a specimen showing an example of a method for monitoring the thickness of a thin film part according to the present invention.
Figure 14:
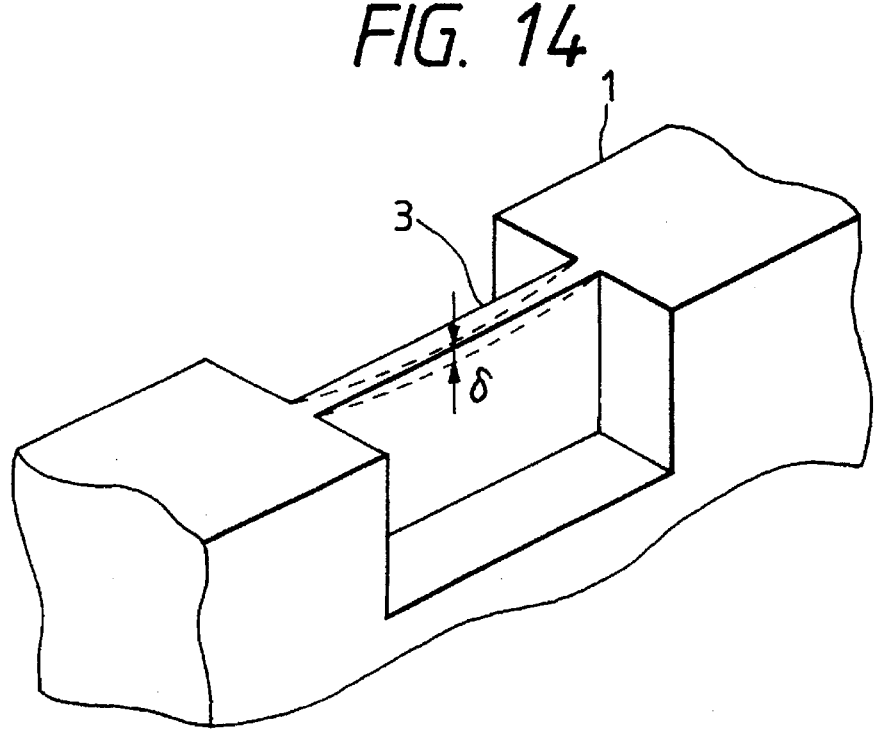
FIG. 14 is a perspective view showing a distortion of the thin film part obtained by milling the specimen.
Figure 15:
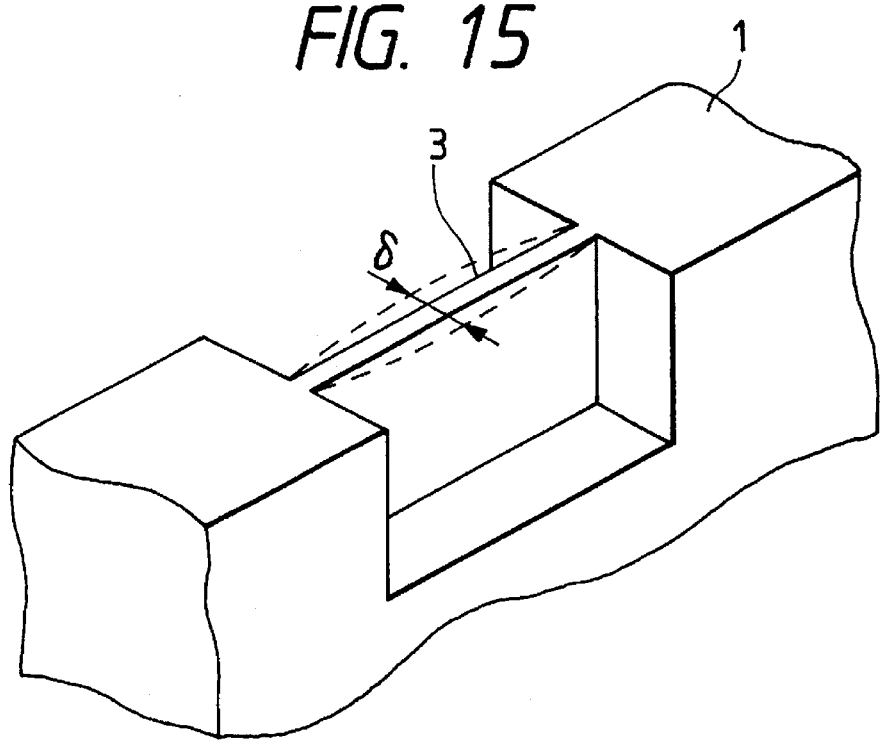
FIG. 15 is a perspective view showing a distortion of the thin film part similarly obtained by milling the specimen.

As shown in FIGS. 13 to 15, a pulse laser beam 15 is irradiated onto the thin film part 3 to heat it and cause a displacement δ due to thermal expansion, as shown in FIG. 14 or 15, and this displacement δ is a function of the thickness. The thickness can be estimated from the displacement by calculating in advance the thickness and the displacement of materials, the shape of the thin film part and an absorption coefficient of the laser beam, or by confirming the values through experiment. For measuring the displacement δ, the probe light beam 7 is reflected at the surface of the thin film part 3 and is made to interfere with the reference light (not shown) reflected at the other fixed portion.

Figure 16A:
FIGS. 16(a) and 16(b) are illustrations showing a current density distribution of the focused ion beam and a sectional shape of the thin film part milled with the focused ion beam.
Figure 16B:
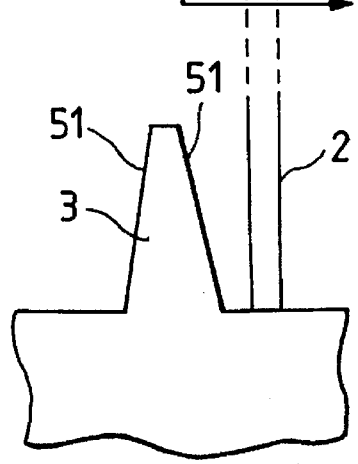
Figure 17:
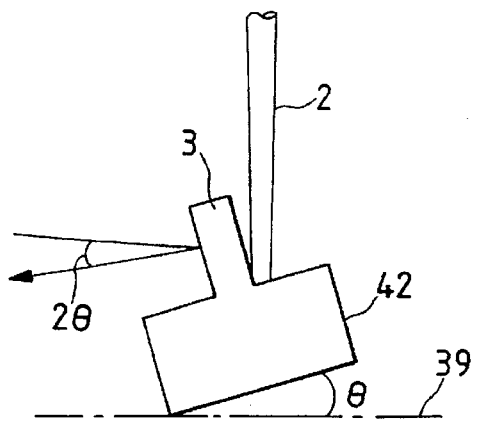
FIG. 17 is a diagrammatic view of a specimen showing a method for milling a tilted specimen according to the present invention.

As shown in FIG. 16(a), the current density distribution has a tail as a curve 50 in milling using a focused ion beam, and therefore the milled surface of the workpiece may be tilted by several degrees due to the effect of the tail, as shown at 51 in FIG. 16(b), even though the laser beam 2 is throttled. For example, if it is assumed that the tilting angle is 2° and the height of the thin film part 3 is 6 μm, a difference of the thickness of approximately 6 μm×tan 2°×2=0.4 μm is found between the upper part and the lower part of the thin film part 3. Thus, a TEM specimen with a uniform thickness cannot be made, and therefore a specimen as shown in FIG. 17 should be tilted in advance by Θ=2° before milling in the above example. However, there is a problem in this case that, when the probe light beam 7 is horizontally directed, the reflected light is tilted by 2Θ and the reflected light does not reach the interferometer located at a distance from the specimen. In a case in which transparent light is used, there is a problem that the length of the light path which passes through the thin film part 3 is extended by as much as $l/\cos\Theta$. Even though the specimen is not tilted, it is difficult to align the probe light beam 7 with the thin film part 3 of approximately 10 μm in thickness.

Figure 18:
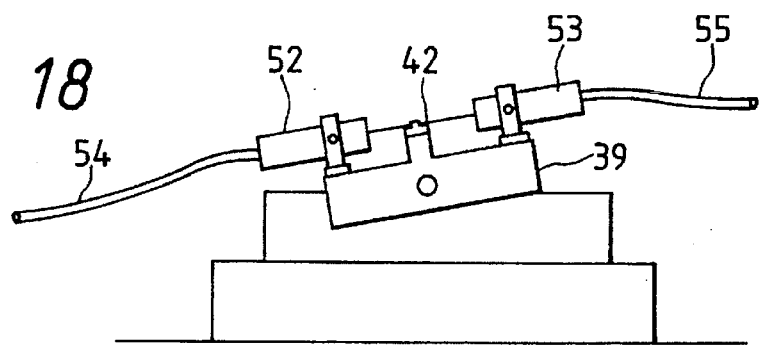
FIG. 18 is a side view of an apparatus showing a light irradiation part and a light receiving part which are mounted on the specimen stage.

As shown in FIG. 18, therefore, it is recommended to attach a lens part 52 for irradiating the probe light beam and a light receiving part 53 of the interferometer for receiving the transparent light from the specimen on a stage 39 and connect an optical fiber 54 and an output cable thereto. The probe light irradiating part 52 and the light receiving part 53 can be positioned in advance at the positions where the thin film part is expected to be formed in the atmosphere. Otherwise, it can be adapted to finely adjust the position of the specimen even after the specimen has been set in the specimen vacuum chamber. In FIG. 18, there are shown the light irradiation part 52 and the light receiving part 53, which are respectively divided into the right and left-side parts. These parts also can be located on the same side of the specimen in the case of a reflected light detector.

Figure 19:
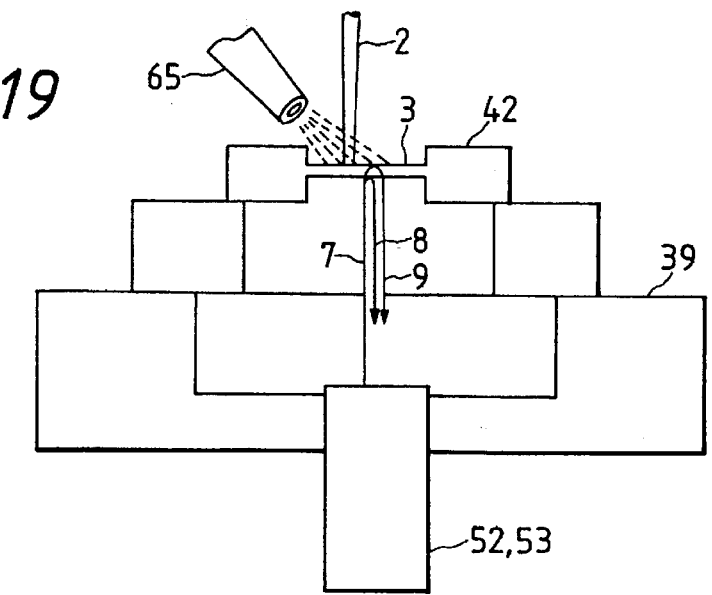
FIG. 19 is a diagrammatic view showing another embodiment of the present invention for milling the specimen by normally irradiating a focused ion beam onto the specimen.

In the above-described embodiments, there is shown an example of a configuration in which the focused ion beam 2 is substantially parallel to the surface of the thin film part 3. As shown in FIG. 19, a method for irradiating the focused ion beam 2 in a direction normal to the thin film part 3 is also available. In this case, the probe light irradiation part 52 and the reflected light receiving part 53 are installed face up. Thus, the thickness of the thin film part 3 can be monitored during milling.

In FIG. 19, a reactive gas from a gas nozzle 65 is blown onto the milled surface to carry out focused ion beam assisted etching. Since an ion having an energy of approximately 30 kV is impinged onto the milled surface in milling with an ion beam, the milled surface is damaged due to ion impact. In the focused ion beam assisted etching, approximately 9/10 of the stock to be milled is removed by chemical reaction with the reactive gas and therefore the ion dose per milling volume is less than in milling only with an ion beam. In other words, the damage due to ion impact is reduced.

Suitable reactive gases for specimens such as Si, $SiO_2$ and SiN include, for example, gases including fluorine, such as $XeF_2$, $SF_6$ and $CF_4$ or gas mixtures, and those for aluminum alloy include gases including chlorine, such as $Cl_2$, $SiCl_4$ and $BCl_3$ or gas mixtures. If a specimen comprises various materials, halogen gas mixtures containing the above gases also are suitable.

It is obvious that focused ion beam assisted etching is equivalently effective not only in impinging of the ion beam in a direction normal to the milled surface, as shown in FIG. 19, but also in slant or horizontal impinging of the ion beam, as shown in FIG. 17.

The following describes a specimen making apparatus according to the present invention, which employs the method for observing marks for measuring the positional drift of the ion beam, compensation of the positional drift of the beam, a thickness monitor for use in milling, and the method for monitoring the tilting angle of the milled surface in the focused ion beam milling machine.

Figure 20:
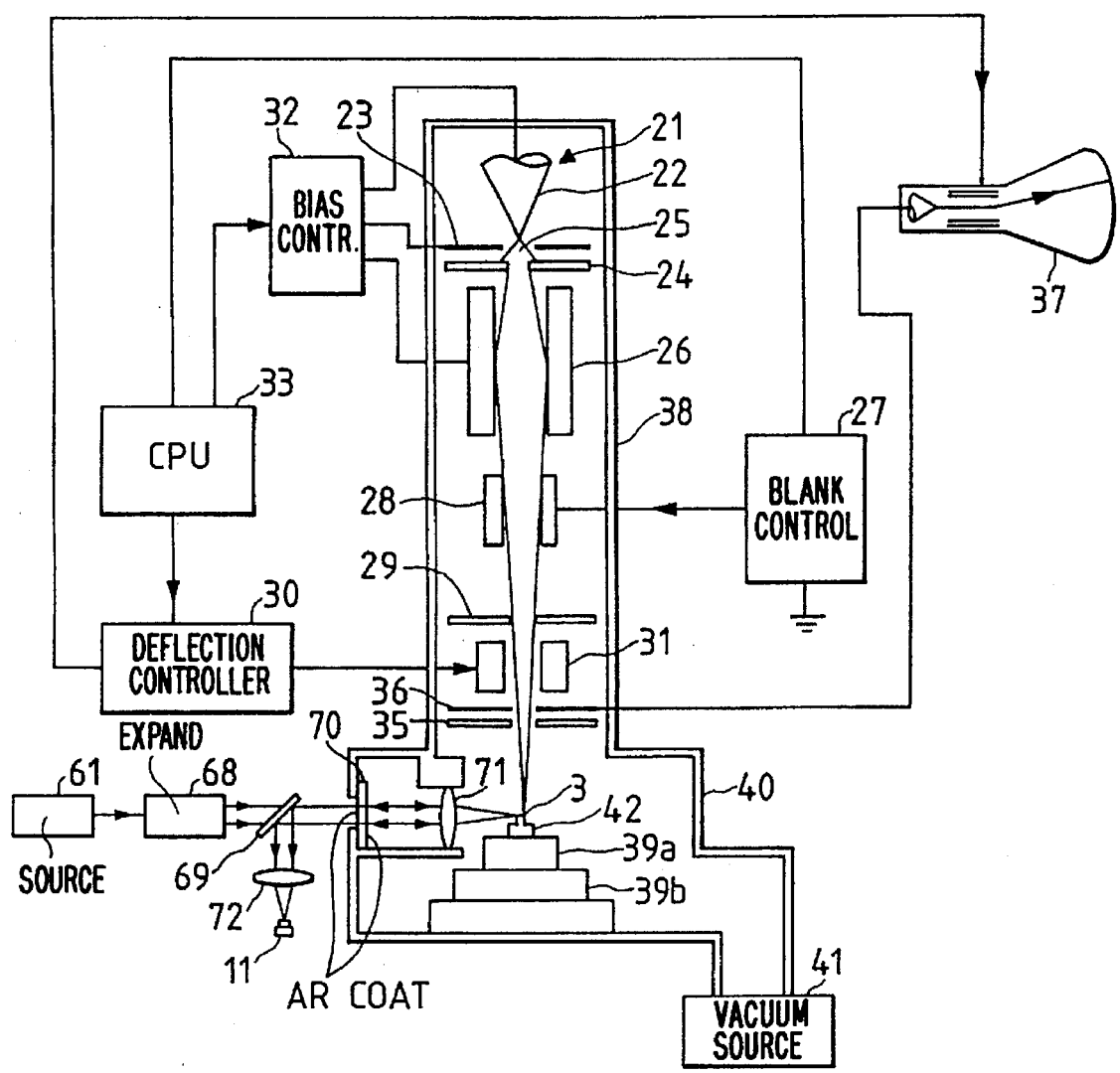
FIG. 20 is a schematic diagram of a principal part of the apparatus according to the present invention provided with a thickness monitor.

FIG. 20 is a schematic sectional view of a main part of an apparatus according to the present invention, which is made up by attaching the interferometer for reflected light, as shown in FIG. 1, to a focused ion beam milling machine.

The main part of the focused ion beam milling machine is described below. In FIG. 20, reference numeral 21 denotes generally ion beam optics which comprise a liquid metal ion source 22, an extractor 23, a defining aperture 24, a electrostatic lens 26 for focusing an ion beam 25 passing through the defining aperture 24, a blanking electrode 28 connected with a blanking power supply 27, a blanking aperture 29, and a deflector 31 connected with a deflection controller 30.

The ion beam optics 21 are housed in a vacuum chamber 38 whereby a focused ion beam 2, which is focused and deflection-controlled by the ion beam optics 21, is supplied to the specimen 42. The specimen 42 is set on stages 39a and 39b, which are arranged to be rotatable around the X and Y axes and movable in parallel to the X and Y axes. The stages 39a and 39b are accommodated in a vacuum chamber 40 and the vacuum chambers 38 and 40 are evacuated to a sufficient level of vacuum by a vacuum pumping system 41.

A control power supply 32 controls the ion source 22, the extractor 23 and the electrostatic lens 26. Reference numeral 33 denotes a computer serving as a controller which is connected to the deflection controller 30, the blanking power supply 27 and the control power supply 32.

Reference numeral 37 denotes an image monitor. A scanning ion image is produced by a micro channel plate (MCP) 35, which detects secondary electrons or secondary charged particles, such as secondary ions, which are emitted from the specimen 42 upon irradiation thereof by the focused ion beam 2, an anode 36 detects a signal from the MCP, and an image monitor 37, operating as a scanning ion microscope image (SIM image) monitor and which is connected with the anode 36 and the deflection controller 30, displays the scanning ion image.

The following describes the construction of a thickness monitor which operates in conjunction with an interferometer for detecting the reflected light. Reference numeral 61 denotes a coherent light source, such as a laser, by which a beam having a wavelength which partly passes through the thin film part 3 of the specimen 42 is generated. A laser beam generated by this coherent light source is expanded by a beam expander 68 and is focused by the focusing lens 71 onto the thin film part 3 of the specimen 42 through a beam splitter 69 and a window (coated with a reflection preventing film) of the vacuum chamber 40. A beam light reflected at the surface of the thin film part 3 and a light beam which passes through the thin film part 3 and is reflected at the opposite surface of the thin film part 3 are reflected by the beam splitter 69 to produce interfering light, which is focused by the focusing lens 72. This interfering light is detected by the interferometer 11, which employs photodetectors, such as photodiodes.

An operating mechanism of this apparatus, according to the present invention, will be described below. In the main part of the focused ion beam milling machine, milling is carried out while compensating for any positional drift of the beam and maintaining the specified relative positions of the milling area with the focused ion beam and the observing area according to the same operating method as previously described using the ion beam optics 21, the X/Y stage 39(a), 39(b), the image monitor 37, and the various controllers. On the other hand, the thickness monitor monitors the thickness of the thin film part during milling and feeds back thickness information to the controller for focused ion beam milling, and thus accurate milling is carried out until the thickness of the thin film part 3 of the specimen reaches the predetermined target thickness.

The above configuration of the apparatus makes it possible to facilitate milling of the specimen for TEM observation, for example, to an extremely thin and uniform thickness in the order of 100 to 200 nm.

Figure 21:
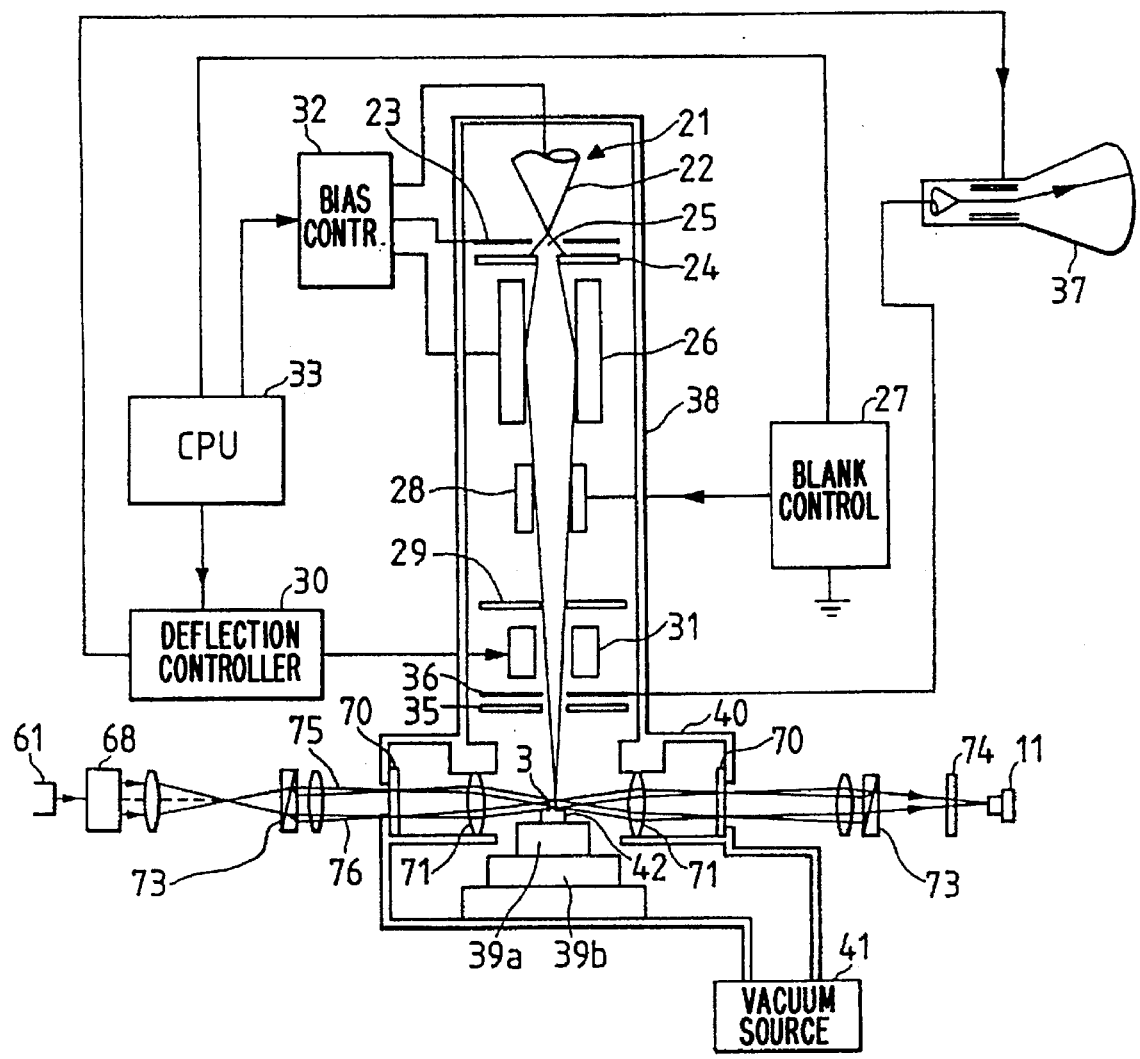
FIG. 21 is a schematic diagram of a principal part of the apparatus according to the present invention provided with another thickness monitor.

FIG. 21 is a schematic sectional view of the main part of the apparatus according to the present invention which is made up by attaching the interferometer for receiving transparent light, as shown in FIG. 8, to the focused ion beam milling machine.

This embodiment has the basically same construction with respect to the optics for focusing the ion beam and the image monitor for observing the image as shown in FIG. 20, and therefore a detailed description of these parts is omitted from the following explanation and the thickness monitor for measuring the thickness of the thin film part 3 being milled is mainly described.

As shown, optics comprising a focusing lens 71 and other elements are constructed so that the beam from the coherent light source 61 is expanded by the beam expander 68 and divided into a P-polarized beam 75 and an S-polarized beam 76 using a Savart plate (double refraction prism) 73 operating through a convex lens, the P-polarized beam passes through the thin film part 3 of the specimen 42 and the S-polarized beam 76 does not pass through the thin film part 3. These beams are combined again into One beam by the Savart plate 73, after passing through the lens 71 and the window 70, and the beams are caused to polarize-interfere by a polarizing plate 74 arranged at the angle of polarization of 45° in reference to the angle of polarization of both beams, and this combined beam is detected by the interferometer 11.

In FIG. 20, though a preferable interference may not be obtained unless the reflectivity and transmissivity of the thin film part are appropriate, the arrangement of FIG. 21 provides an effect that such preferable interference may be easily obtained even though the reflectivity is low.

Figure 22:
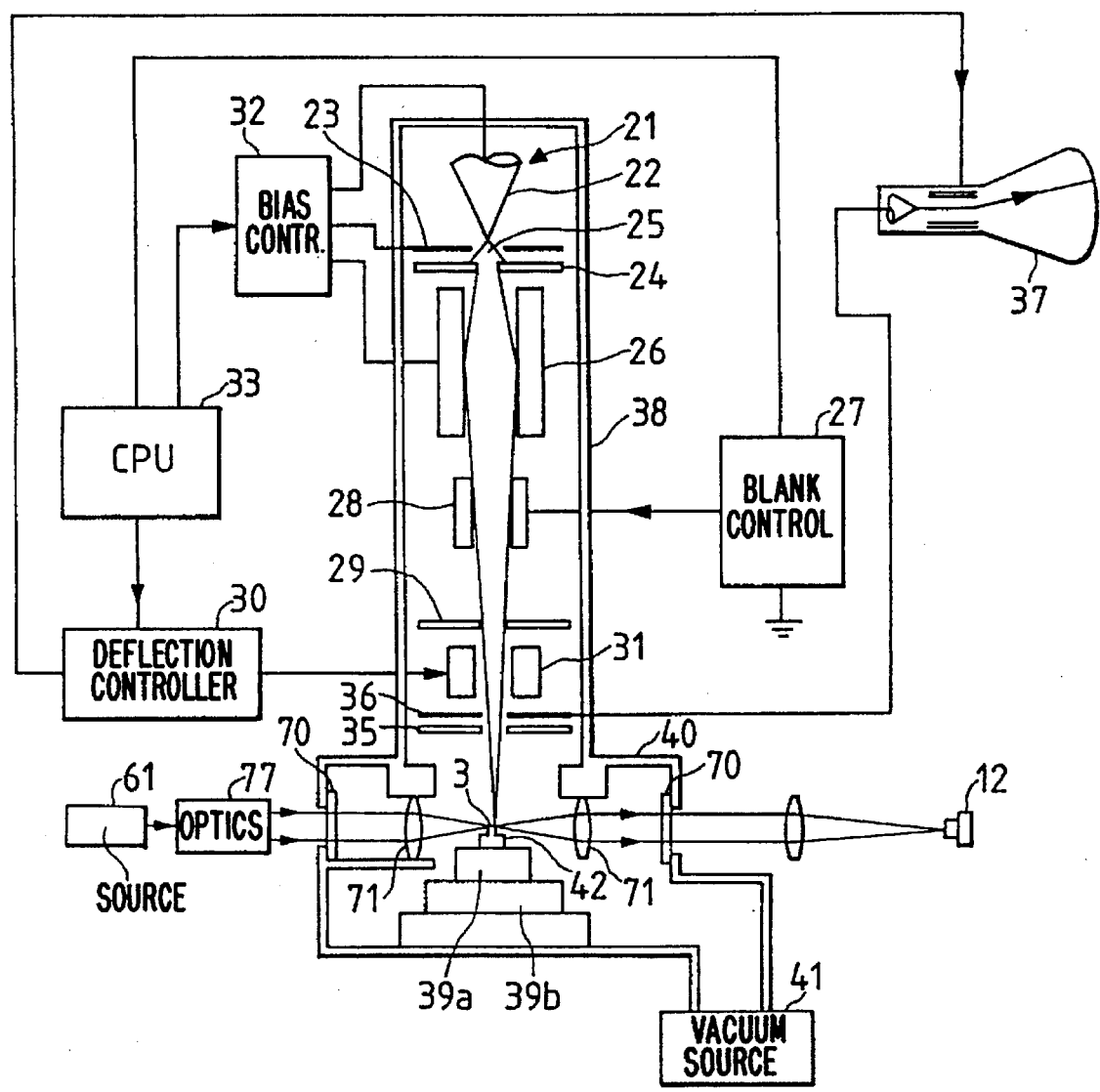
FIG. 22 is a schematic diagram of a principal part of the apparatus according to the present invention provided with a further thickness monitor.

FIG. 22 is a schematic view of the main part of the apparatus according to the present invention made up by attaching the photodetector for the transparent light shown in FIG. 9 to a focused ion beam milling machine.

This embodiment also has basically the same construction with respect to the optics for focusing the ion beam and the image monitor for observing the image as in the embodiment shown in FIG. 20, and therefore a description of these parts is omitted from the following explanation and the thickness monitor for measuring the thickness of the thin film part 3 being milled is mainly described.

As shown, this embodiment of the thickness monitoring optics is adapted to cause the beam from the coherent light source 61 (a laser beam source can also be used) to pass through the thin film part 3 of the specimen 42 after passing through the collimating optics 77, the window 70 and the focusing lens 71, and to detect a degree of absorption of light of the thin film part using the photodetector 12.

Though it is necessary to provide the beam splitter in FIG. 20, this beam splitter is not required in this embodiment and therefore it is advantageous in that the apparatus is inexpensive and adjustment of the apparatus is easy.

Figure 23A:
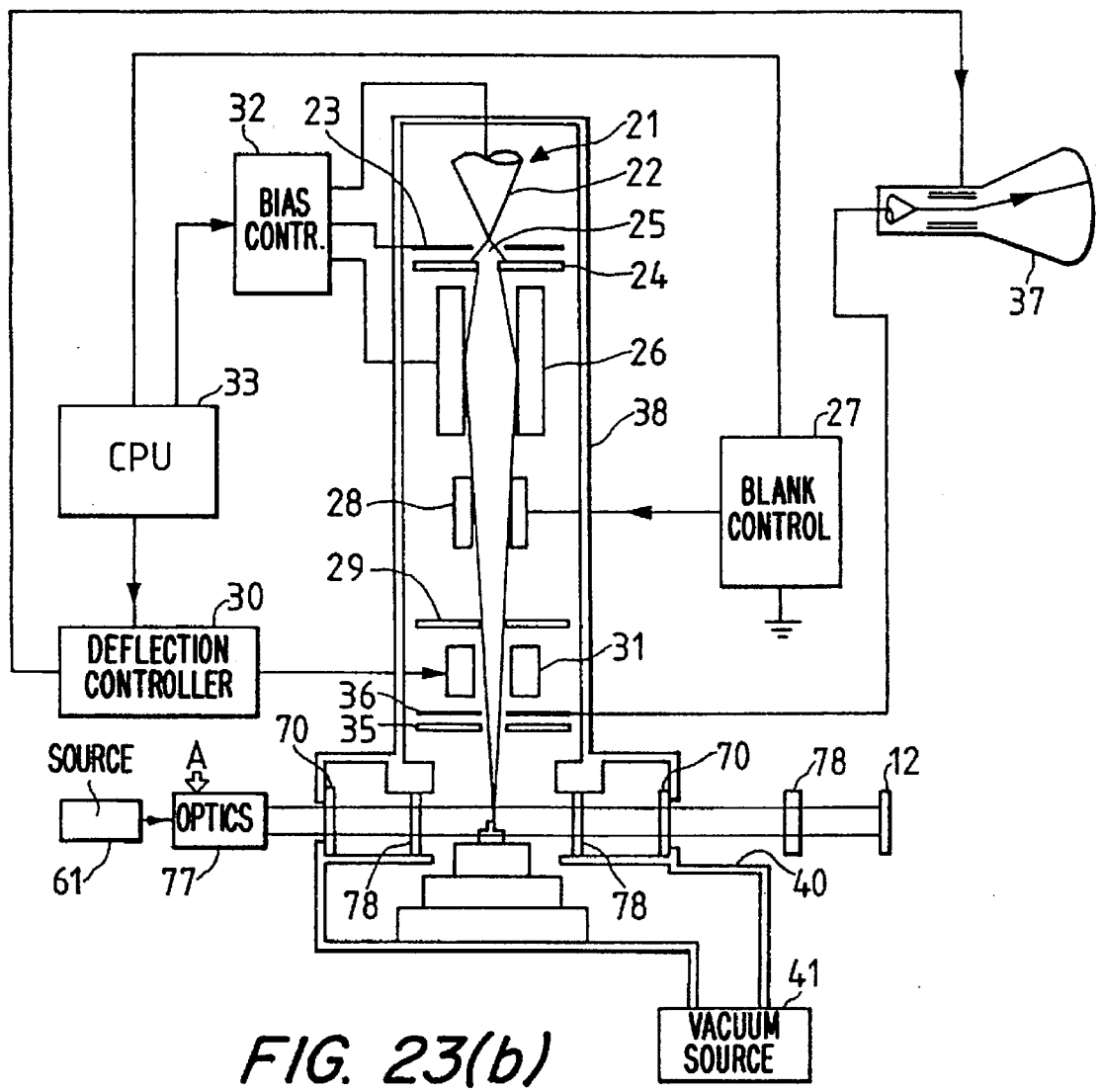
FIG. 23 (a) is a schematic diagram of a principal part of the apparatus according to the present invention provided with still another thickness monitor.
FIG. 23(b) is a schematic diagram of the optical path taken in the direction of arrow A in FIG. 23(a)

FIG. 23(a) is a schematic diagram of the main part of an apparatus according to the present invention made up by attaching the photodetector for the transparent slit-shaped beam shown in FIG. 11 to a focused ion beam milling machine.

This example also has basically the same construction with respect to the optics for focusing the ion beam and the image monitor for observing the image as in the embodiment shown in FIG. 20 and therefore the description of these parts is omitted from the following explanation and the thickness monitor for measuring the thickness of the thin film part 3 being milled is mainly described.

Figure 23B:
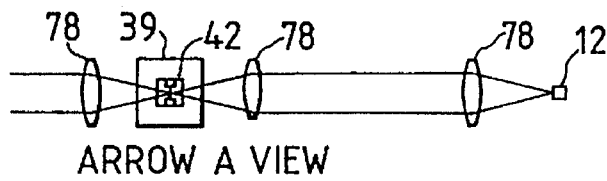

As shown, this embodiment of the thickness monitoring optics is adapted to cause the beam from the light source 61, as a slit-shaped beam, to pass through the thin film part 3 of the specimen 42 after passing through the collimating optics 77, the window 70 and the cylindrical lens 78, to focus this slit-shaped beam onto the photodetector 12 comprising a photodiode array (for example, CCD sensor) through two cylindrical lenses 78, as seen in FIG. 23(b), and to measure the distribution of light absorption of the thin film part (a distribution along the longitudinal direction of the slit-shaped beam).

Though it is difficult to obtain the thickness distribution of the thin film part (for example, thin at the upper part and thick at the lower part) in FIGS. 20 to 22, this embodiment makes it possible to check the thickness distribution in the vertical direction of the thin film part, and therefore, if the thickness distribution is unsatisfactory, adjustment can be made easily by adjusting the irradiation angle of the ion beam.

Figure 24:
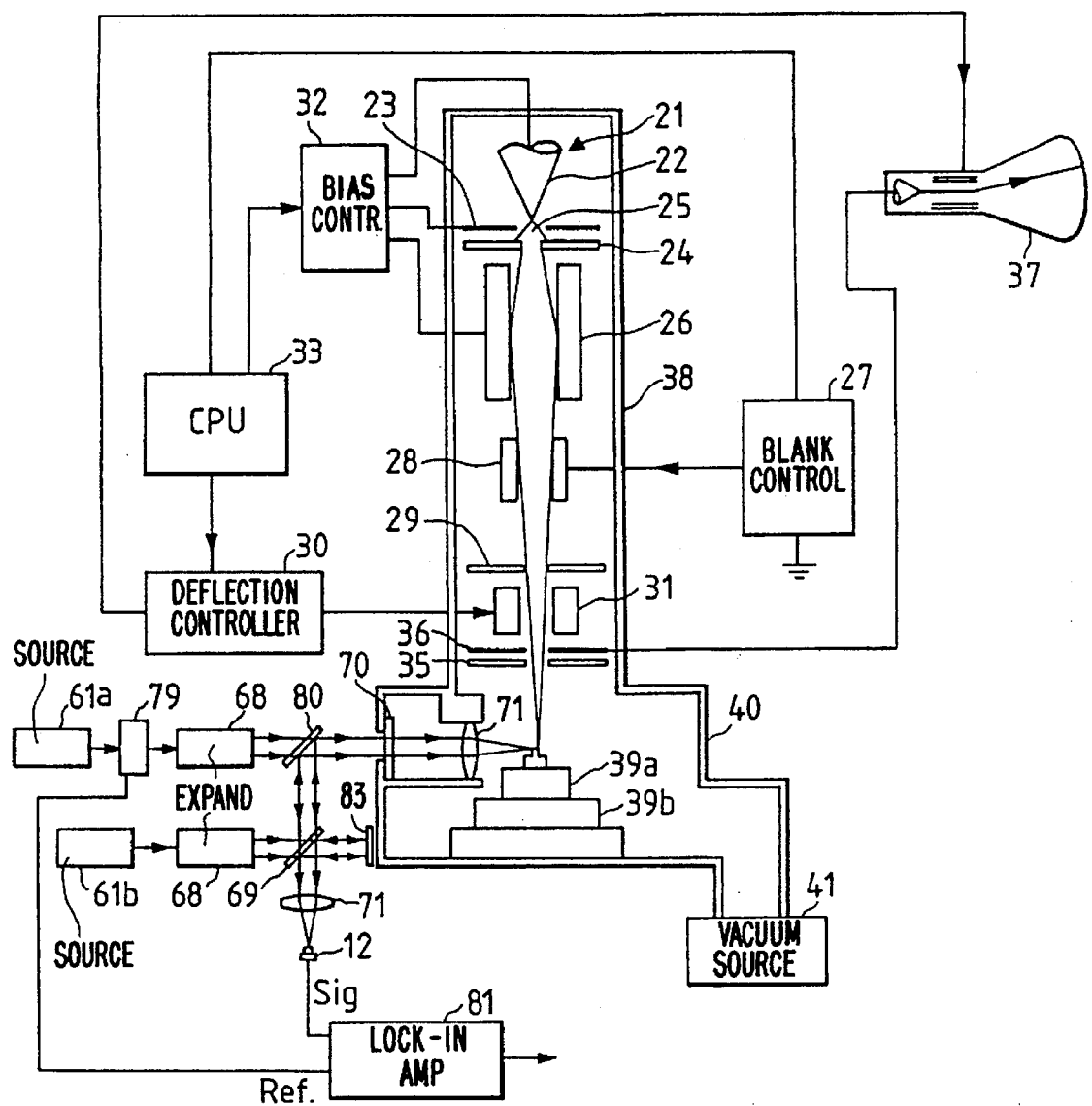
FIG. 24 is a schematic diagram of a principal part of the apparatus according to the present invention provided with a still further thickness monitor.

FIG. 24 is a schematic diagram of the main part of an apparatus according to the present invention made up by attaching a device for precisely measuring distortion or thermal expansion of the thin film part 3, as seen in FIGS. 14 and 15, when an intensity modulated laser beam is irradiated, by using interference of the laser beam with the focused ion beam in the milling machine.

This embodiment also has basically the same construction with respect to the optics for focusing the ion beam and the image monitor for observing the image as in the embodiment shown in FIG. 20 and therefore the description of these parts is omitted from the following explanation and the thickness monitor for measuring the thickness of the thin film part 3 being milled is mainly described.

As shown, this embodiment of the thickness monitoring optics is adapted to expand the beam, such as a laser beam emitted from the light source 61a, through the beam expander 68, after the intensity of the beam has been modulated with a specified frequency by a chopper 79, such as an acoustic-optic modulator, to focus the beam using the focusing lens 71 and to irradiate it onto the thin film part 3 of the specimen 42 after passing through a dichroic mirror 80 and the window 70. At the thin film part, a cyclic displacement is produced due to thermal expansion synchronized with the above intensity modulated frequency.

On the other hand, a beam, such as the laser beam emitted from the coherent light source 61b, is expanded by a beam expander 68 and is separated into two beams by the beam splitter 69. One of these beams is reflected at the dichroic mirror 80 and is focused and irradiated by the focusing lens 71 onto the same position as the focusing part of the above intensity modulated light on the thin film part 3 of the specimen 42 through the window 70. The reflected light and the reference light separated by the above beam splitter 69 and reflected by a reference mirror 83 are made to interfere each other and the interfered light is focused by the focusing lens 71 and detected by the interferometer 12 using a photodetector, such as a photodiode. The detection signal is sent to a synchronous demodulation circuit, such as a lock-in amplifier 81, and the amplitude and phase of a thermal expansion component are extracted with the intensity modulated signal as a reference signal.

This embodiment provides an effect that, though the light which passes through the thin film part is not used in the manner shown in FIGS. 20 to 22, the displacement due to thermal expansion which results from absorption of the light can be obtained even when the transmissivity of light of the thin film part is low and the transparent light intensity is insufficient, and therefore the thickness of the thin film part can be known.

Figure 25:
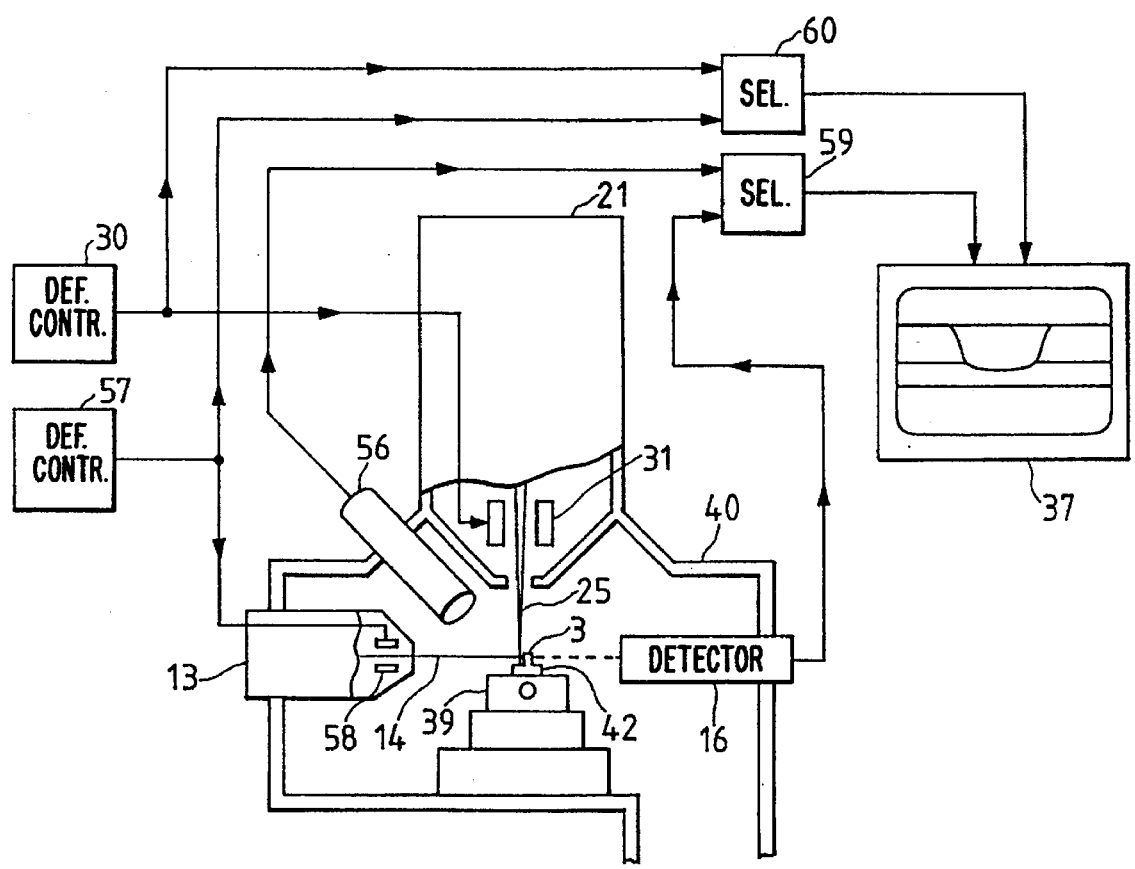
FIG. 25 is a schematic diagram of a principal part of the apparatus according to the present invention provided with yet another thickness monitor.

FIG. 25 is a schematic diagram of the main part of an apparatus according to the present invention made up by attaching a device for measuring a transparent electron beam shown in FIG. 12 to a focused ion beam milling machine.

Figure 3:
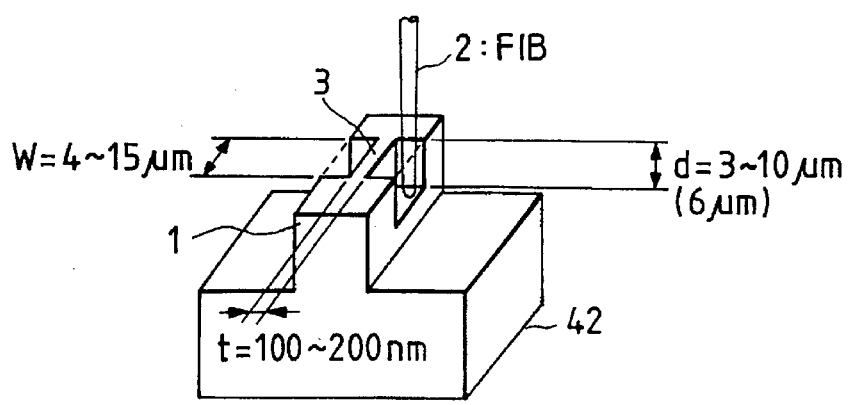
FIG. 3 is a perspective view showing an example of a conventional specimen making method.

As shown, the specimen chamber 40 is provided with the focused ion beam optics 21, the electron beam gun 13, a secondary electron beam detector 56, a detector 16 for detecting the electron beam which passes through the specimen, and the stage 39. The specimen 42 to be milled as shown in FIG. 3 is set on the stage 39. The focused ion beam 25 for milling the specimen 42 is deflection-scanned by applying signals from the deflection controller 30 to the deflector 31.

The electron beam 14 is deflection-scanned by applying signals from a deflection controller 57 to a deflector 58.

Secondary electrons obtained by irradiation of the focused ion beam 25 and secondary electrons obtained by irradiation of the electron beam 14 are detected by the secondary electron detector 56, and the secondary electron image obtained from irradiation of the focused ion beam 25 is used for observing the top view of the specimen 42, and the secondary electron image obtained from irradiation of the electron beam 14 is used for observing the cross section of the thin film part of the specimen.

The electron beam which has passed the thin film part 3 of the specimen 42 is detected by the electron beam detector 16 and is used for measuring the thickness or the thickness distribution of the thin film.

The output of the secondary electron detector 56 and the output of the electron beam detector 16 are supplied to an electron beam output selector 59. In this selector 59, a low frequency pass filter and a high frequency pass filter are provided as described later. Electron beam deflection signals and focused ion beam deflection signals are supplied to a deflection signal selector 60.

For observing the scanning ion microscope image (SIM image) using these selectors 59 and 60, the ion beam deflection signal and the secondary electron detection output are applied to the image monitor 37.

For observing the scanning electron microscope image (SEM image), the electron beam deflection signal and the secondary electron detection output are applied to the image monitor 37.

For observing the intensity distribution of the transparent electron beam, the electron beam deflection signal and the transparent electron beam detection output are supplied to the image monitor 37.

The detector for obtaining the scanning ion microscope image may be a micro channel plate 35 as shown in FIG. 20. Though one image monitor 37 is used in FIG. 25 to reduce the cost of the whole apparatus, the configuration need not be limited to this and the scanning ion microscope image, the scanning electron microscope image and the transparent electron beam image can be observed on respective dedicated image monitors by providing two or more image monitors.

Two types of beams, that is, the focused ion beam 25 and the electron beam 14 can be supplied simultaneously or separately at delimited timings. By supplying these beams simultaneously, the scanning electron microscope images (SEM images) of the cross sectional views of the milled surface can be simultaneously observed while milling the specimen with the ion beam.

Figure 26A:
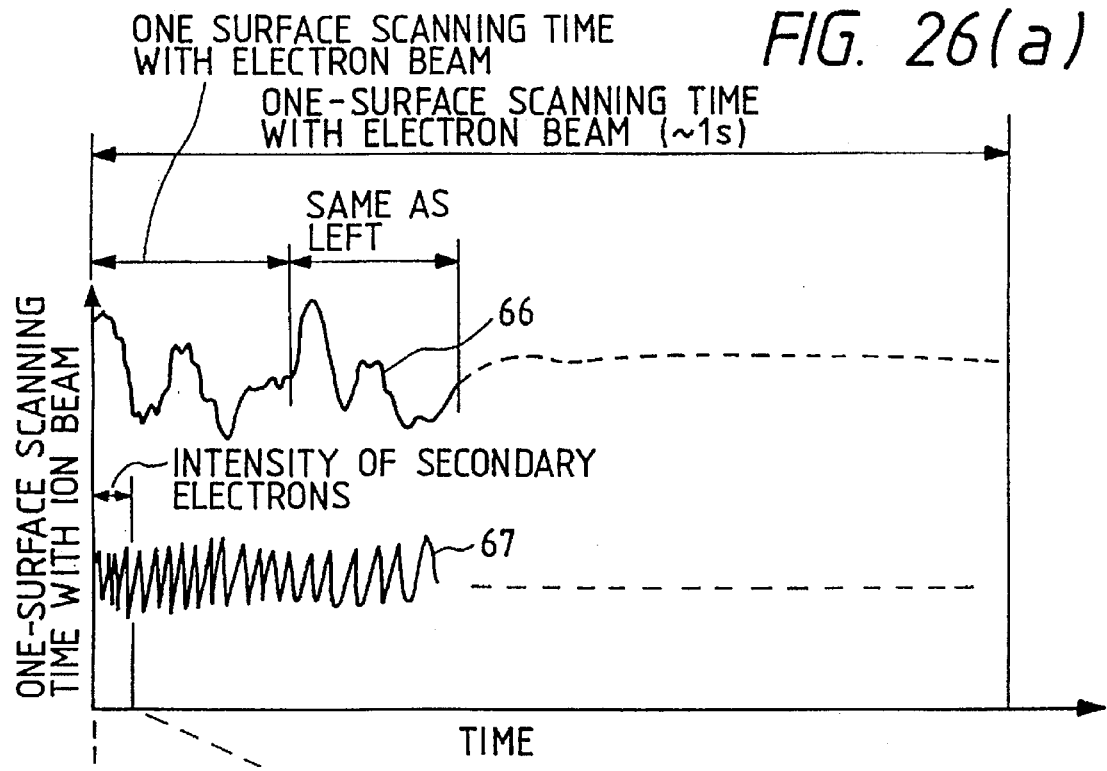
FIGS. 26(a) and 26(b) are graphs representing a variation of a secondary electron signal with respect to time.

In case two image monitors 37 are provided, the SEM image and the SIM image can be simultaneously observed. However, in case of simultaneous scanning, the secondary electron signal to be detected by the secondary electron detector 56 is a secondary electron signal 66 obtained with the electron beam, which is superposed with a secondary electron signal 67 obtained with the focused ion beam, as shown in FIG. 26(a), and therefore, if the SEM image and the SIM image are displayed by using this secondary electron signal, the image being displayed includes many noises.

Figure 26B:
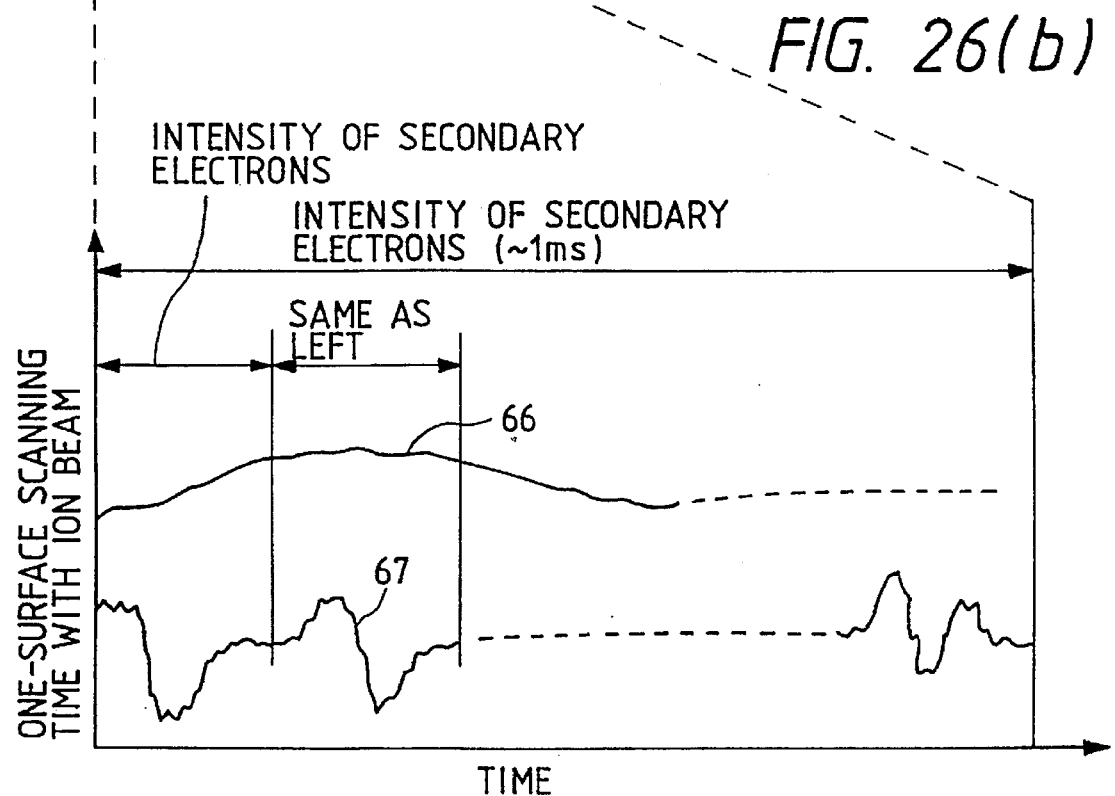

With respect to the scanning velocity, the focused ion beam is scanned at a high scanning velocity of, for example, 1 ms for one surface, since the milled surface in focused ion beam milling can be finished more smoothly at the higher scanning velocity, while the electron beam can be scanned at a low scanning velocity of, for example, approximately 1 s for one surface. As shown in FIG. 26(b), therefore, the signal 66 obtained with the electron beam mainly comprises a low frequency component and the signal 67 obtained with the focused ion beam mainly comprises a high frequency component.

For obtaining a SEM image using a filter (not shown) provided in the selector 59, secondary electron signals which pass through the low frequency pass filter are used, and, for obtaining the SIM image, secondary electron signals which pass through the high frequency pass filter are used. Thus, satisfactory SEM and SIM images can be obtained.

This method is effective to check the progress of milling more precisely and obtain a more satisfactory finishing performance, since the focused ion beam milling can be carried out while observing the cross sectional SEM image, not only in making a specimen for TEM observation, but also in milling a specimen for SEM observation of the cross-section.

Figure 27:
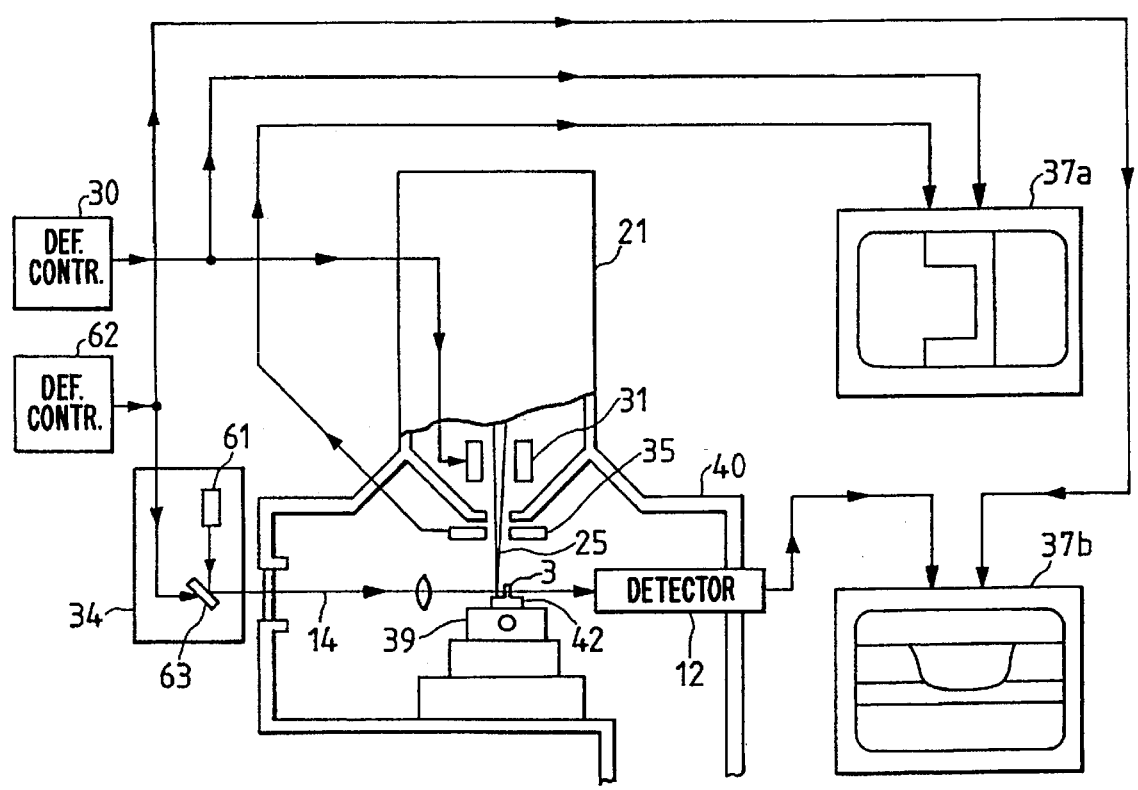
FIG. 27 is a schematic diagram of a principal part of the apparatus according to the present invention provided with another thickness monitor.

FIG. 27 is a schematic diagram of the main part of an apparatus according to the present invention made up by attaching a device for obtaining a scanning transparent light image by particularly scanning a focused probe light, in a method for measuring the transparent light shown in FIG. 9, to a focused ion beam milling machine.

This embodiment also has basically the same construction with respect to the optics for focusing the ion beam and the image monitor for observing the image as in the embodiment shown in FIG. 20, and therefore the description of these parts is omitted from the following explanation and the thickness monitor for measuring the thickness of the thin film part 3 being milled is mainly described.

As shown, the specimen chamber 40 is provided with the focused ion beam optics 21, laser beam focusing optics 34 (incorporating a laser beam source 61 and a galvanometer 63), the MCP 35 for detecting secondary ions, the detector 12 for detecting the laser beam passing through the specimen 42, and the stage 39. The specimen 42 is placed on the stage 39.

The probe light 14 of the laser beam is deflection-scanned by applying signals from the laser beam deflection controller 62 to the galvanometer 63. The laser beam which has passed through the thin film part 3 of the specimen 42 is detected by the light detector 12. The deflection signal from the laser beam deflection controller 62 and the transparent light intensity signal from the light detector 12 are supplied to the image monitor 37b, whereby the scanning transparent image is displayed and the thickness distribution of the thin film part can be known. On the other hand, the SIM image is displayed on the image monitor 37a in the same manner as in FIG. 25 and the surface of the specimen can be observed.

The above configuration of the apparatus makes it possible to observe the transparent light image of the milled thin film part while milling the specimen surface with the focused ion beam, and therefore it is easy to determine the milled thickness of the thin film part.

According to the embodiments of the present invention, the milled thickness distribution (only in the vertical direction in FIG. 23) of the thin film part can be checked both in the vertical and horizontal directions even during milling and the irradiating position and angle of the ion beam can be finely adjusted, and therefore a unique effect can be attained in which a high efficiency of precision milling is obtained with a high percentage of success.

As described in detail, the present invention makes it possible to implement the anticipated objects. Specifically, the thin film part can be prevented from being irradiated with the focused ion beam during observation of the marks provided on the specimen as the SIM image, and therefore the thin film part can be milled with high preciseness even though a positional drift of the focused ion beam occurs. In addition, an appropriate infeed amount can be set even with an inexpensive apparatus by using a light beam as means for monitoring the thickness of the thin film part during milling. The present invention provides an effect that, since the thickness distribution of the thin film part to be milled with the light beam or an electron beam can be measured, the TEM specimen can be finished to an appropriate thickness within a short period of time and with a high percentage of success and the efficiency of TEM observation can be strikingly raised.

What is claimed is:

1. A method of making a specimen for observation through a transparent electron microscope, comprising the steps of:

milling part of the specimen to form a thin film part, which can be observed through a transparent electron microscope, by scanning and irradiating a focused ion beam onto the specimen;

observing a mark for detection of position provided on said specimen as a secondary charged particle image, by scanning and irradiating said focused ion beam onto said specimen without irradiating said focused ion beam onto said portion to be milled into said thin film part during said step of milling;

detecting positional drift of said focused ion beam during said step of milling in accordance with a result of said observation of said mark for detection of position in relation to said milled part compensating for said detected positional drift; and monitoring the thickness of a portion, which is milled into a thin film part by said focused ion beam, during milling of said specimen to enable milling of said portion into said thin film part to a predetermined specified thickness by monitoring said thickness.

2. A method of making a specimen according to claim 1, wherein said monitoring of the thickness is carried out by an optical interference technique.

3. A method of making a specimen according to claim 1, wherein said monitoring of the thickness is carried out by utilizing a light beam.

4. A method of making a specimen according to claim 1, wherein said monitoring of the thickness is carried out by utilizing an electron beam.

5. A method of making a specimen according to claim 1, wherein said monitoring of the thickness is carried out by detecting a transparent image of a scanning laser beam directed at said specimen.

6. A method of making a specimen according to claim 1, wherein said monitoring of the thickness is carried out by detecting a transparent amount of an electron beam directed at said specimen.

7. A method of making a specimen according to claim 1, wherein said monitoring of the thickness is carried out by detecting a transparent image of a scanning electron beam directed at said specimen.

8. A method of making a specimen according to claim 1, wherein said monitoring of the thickness is carried out by detecting distortion of the thin film part due to irradiation of the specimen by a pulse laser beam.

9. A method of making a specimen for observation through a transparent electron microscope, comprising the steps of:

milling part of the specimen to form a thin film part, which can be observed through a transparent electron microscope, by scanning and irradiating a focused ion beam onto the specimen;

observing a mark for detection of position provided on said specimen as a secondary charged particle image, by scanning and irradiating said focused ion beam onto said specimen without irradiating said focused ion beam onto said portion to be milled into said thin film part during said step of milling;

detecting positional drift of said focused ion beam during said step of milling in accordance with a result of said observation of said mark for detection of position in relation to said milled part;

compensating for said detected positional drift; and monitoring a tilting angle of the milled surface of said thin film part during milling of said thin film part by said focused ion beam.

10. A method of making a specimen according to claim 9, wherein monitoring of said tilting angle of the milled surface of the thin film part is carried out by measuring an angle of reflection of a light beam irradiated onto said milled surface.

11. A method of making a specimen for observation through a transparent electron microscope, comprising the steps of:

milling part of the specimen to form a thin film part, which can be observed through a transparent electron microscope, by scanning and irradiating a focused ion beam onto the specimen;

observing a mark for detection of position provided on said specimen as a secondary charged particle image, by scanning and irradiating said focused ion beam onto said specimen without irradiating said focused ion beam onto said portion to be milled into said thin film part during said step of milling;

detecting positional drift of said focused ion beam during said step of milling in accordance with a result of said observation of said mark for detection of position in relation to said milled part;

compensating for said detected positional drift; and using an electron beam to monitor a thickness of a portion of said specimen which is milled to form the thin film part, said electron beam being scanned and irradiated onto said specimen, without irradiating said electron beam onto said portion to be milled into said thin film part, at a scanning velocity which largely differs from a scanning velocity of said focused ion beam, detecting secondary charged particles generated from said specimen by said irradiation, filtering a signal of said detected secondary charged particles through a filter to eliminate noise, and displaying a scanning electron microscope image or a scanning ion microscope image by using said secondary charged particle signal from which noise is eliminated.

12. An apparatus for making a specimen for observation through a transparent electron microscope, comprising:

a high brightness ion source for generating a high brightness ion beam;

ion beam irradiation means for focusing said generated high brightness ion beam to an extremely small spot and for scanning and irradiating said focused high brightness ion beam onto the specimen for milling a surface of said specimen to a thin film part which is observable through a transparent electron microscope;

secondary charged particle detection means for detecting secondary charged particles generated from said specimen by irradiation of said specimen by said focused ion beam including an area of said specimen on which a mark for detecting a milling position of said specimen is formed;

secondary charged particle image displaying means for displaying a secondary charged particle image according to a detection signal of said secondary charged particles detected by said secondary charged particle detection means;

irradiation area control means for limiting irradiation by said focused ion beam during milling to an area of said specimen other than said area of said specimen on which said mark for detecting a milling position of said specimen is formed and displayed by said secondary charged particle image displaying means;

detecting means for detecting positional drift of said focused ion beam during milling in accordance with said mark for detecting said milling position on the surface of said specimen displayed by said secondary charged particle image displaying means in relation to said milled specimen surface; and compensating means for compensating for said detected positional drift.

13. An apparatus for making a specimen according to claim 12, further comprising thickness measuring means for measuring a thickness of the portion of said specimen which is milled into said thin film part during milling of said specimen.

14. An apparatus for making a specimen apparatus according to claim 13, wherein said thickness measuring means comprises a light irradiating part for irradiating a light beam onto the portion milled into said thin film part and an interferometer for detecting an interference light which occurs at the portion milled into said thin film part with the light beam irradiated from said light irradiating part.

15. An apparatus for making a specimen according to claim 13, wherein said thickness measuring means comprises a light irradiating part for irradiating a light beam onto the portion milled into said thin film part and a transparent light intensity detector for detecting the intensity of the light beam which has been irradiated from said light irradiating part and has passed through the portion being milled into said thin film part.

16. An apparatus for making a specimen according to claim 13, wherein said thickness measuring means comprises a slit-shaped light irradiating part for irradiating a slit-shaped light beam onto the portion milled into said thin film part and a transparent light intensity detector for detecting the intensity of the light beam which has been irradiated from said slit-shaped light irradiating part and has passed through the portion being milled into said thin film part.

17. An apparatus for making a specimen according to claim 13, wherein said thickness measuring means comprises a laser beam irradiating part for irradiating a laser beam onto the portion being milled into said thin film part, a transparent laser intensity detector for detecting the intensity of the laser beam which has been irradiated from said laser beam irradiating part and has passed through the portion being milled into said thin film part, and a transparent image displaying part for displaying a transparent image of the portion which has been milled into said thin film part with said laser beam detected by said transparent laser beam intensity detector.

18. An apparatus for making a specimen according to claim 13, wherein said thickness measuring means comprises an electron beam irradiating part for scanning and irradiating an electron beam onto the portion being milled into said thin film part, a transparent electron beam intensity detector for detecting the intensity of the electron beam which has been irradiated from said electron beam irradiating part and has passed through the portion being milled into said thin film part, and a transparent scanning electron microscope image displaying unit for displaying a transparent image of the portion which has been milled into said thin film part with said electron beam detected by said transparent electron beam intensity detector.

19. An apparatus for making a specimen according to claim 13, wherein said thickness measuring means comprises a pulse laser irradiating part for irradiating a pulse laser onto the portion being milled into said thin film part and a detector for detecting distortion of the portion being milled into said thin film part, said distortion being caused by irradiating the pulse laser thereto from said pulse laser irradiating part.

20. An apparatus for making a specimen according to claim 13, wherein the thickness measuring means includes means for providing a light beam to enable thickness measuring.

21. An apparatus for making a specimen according to claim 13, wherein the thickness measuring means includes means for providing an electron beam to enable thickness measuring.

22. An apparatus for making a specimen according to claim 12, further having tilting angle measuring means for measuring a tilting angle of the surface of said specimen being milled into said thin film part during milling of said specimen.

23. An apparatus for making a specimen according to claim 22, wherein said tilting angle measuring means comprises a light irradiating part for irradiating a light beam onto the portion milled into said thin film part and a detector for detecting a reflecting position of light reflected at said milled surface.

24. An apparatus for making a specimen for observation through a transparent electron microscope, comprising:
a high brightness ion source for generating a high brightness ion beam;
ion beam irradiation means for focusing said generated high brightness ion beam to an extremely small spot and for scanning and irradiating said focused high brightness ion beam onto specimen for milling a surface of said specimen to a thin film part which is observable through a transparent electron microscope;
electron beam irradiation means for focusing an electron beam and for scanning and irradiating said electron beam onto said specimen;
secondary charged particle detection means for separately detecting secondary charged particles generated from said specimen by irradiation of said specimen by said focused ion beam and said focused electron beam;
secondary charged particle image displaying means for displaying a secondary charged particle image according to a detection signal of said secondary charged particles detected by said secondary charged particle detection means;
irradiation area control means for limiting irradiation of said focused ion beam during milling to a milling area of said specimen, so that a surface of the specimen to be milled into said thin film part in said milling area is not included in an observing area where said secondary charged particle image is obtained on the surface of said specimen, when said focused ion beam is respectively irradiated onto the milling area where a part of said specimen is milled into the thin film part by said focused ion beam;
detecting means for detecting positional drift of said focused ion beam in accordance with said secondary charged particle image on the surface of said specimen in relation to said milled part; and
compensating means for compensating for said detected positional drift.

25. An apparatus for making a specimen for observation through a transparent electron microscope, comprising:
a high brightness ion source for generating a high brightness ion beam;
ion beam irradiation means for focusing said generated high brightness ion beam to an extremely small spot and for scanning and irradiating said focused high brightness ion beam onto specimen for milling a surface of said specimen to a thin film part;
electron beam irradiation means for focusing an electron beam and for scanning and irradiating said electron beam onto said specimen;
secondary charged particle detection means for detecting secondary charged particles generated from said specimen by irradiation of said specimen by said focused ion beam and/or said focused electron beam;
secondary charged particle image displaying means for displaying a secondary charged particle image according to a detection signal of said secondary charged particles detected by said secondary charged particle detection means;
irradiation area control means for limiting irradiation of said focused ion beam during milling to a milling area of said specimen, so that a surface of the specimen to be milled into said thin film part in said milling area is not included in an observing area where said secondary charged particle image is obtained on the surface of said specimen, when said focused ion beam is respectively irradiated onto the milling area where a part of said specimen is milled into the thin film part by said focused ion beam;
detecting means for detecting positional drift of said focused ion beam in accordance with said secondary charged particle image on the surface of said specimen in relation to said milled part;
compensating means for compensating for said detected positional drift; and
transparent electron beam intensity detection means for detecting the electron beam which has been scanned and irradiated by said electron beam irradiation means and has passed through said specimen, and transparent scanning electron microscope image displaying means for displaying a transparent image of said specimen according to said electron beam detected by said transparent electron beam intensity detection means.

26. A method of making a specimen for observation through a transparent electron microscope, comprising the steps of:
milling part of the specimen to form a thin film part which is observable through a transparent electron microscope by scanning and irradiating a focused ion beam onto said specimen;

scanning and irradiating an electron beam onto said specimen to observe a surface of the thin film part of said specimen with a different scanning speed from that of said focused ion beam;

displaying a secondary charged particle image of said focused ion beam and of said electron beam, in which signals of secondary charged particles of said focused ion beam and of said electron beam are filtered to eliminate noise;

detecting positional drift of said focused ion beam during said step of milling in accordance with a result of said observation of said surface for detection of position in relation to said milled part; and compensating for said detected positional drift.

27. A method of making a specimen according to claim 26, wherein said focused ion beam and said electron beam simultaneously irradiate said specimen.

* * * * *